US012682578B2

(12) United States Patent (10) Patent No.: US 12,682,578 B2

Shelton, IV et al. (45) Date of Patent: Jul. 14, 2026

(54) SYSTEMS AND METHODS FOR CHANGING DISPLAY OVERLAY OF SURGICAL FIELD VIEW BASED ON TRIGGERING EVENTS

(71) Applicant: Cilag GmbH International, Zug (CH)

(72) Inventors: Frederick E. Shelton, IV, Hillsboro, OH (US); Jacqueline C. Aronhalt, Loveland, OH (US); Shane R. Adams, Lebanon, OH (US); Cory G. Kimball, Hamilton, OH (US); Monica L. Z. Rivard, Cincinnati, OH (US); Leonardo N. Rossoni, Rahway, NJ (US); Matthew D. Cowperthwait, Cincinnati, OH (US); Risto Kojcev, Santa Clara, CA (US); Felix J. Bork, Schnürpflingen (DE)

(73) Assignee: Cilag GmbH International, Zug (CH)

( * ) Notice: Subject to any disclaimer, the term of this patent is extended or adjusted under 35 U.S.C. 154(b) by 628 days.

(21) Appl. No.: 17/688,633

(22) Filed: Mar. 7, 2022

(65) Prior Publication Data

US 2022/0331050 A1 Oct. 20, 2022

Related U.S. Application Data

(60) Provisional application No. 63/284,326, filed on Nov. 30, 2021, provisional application No. 63/174,674, filed on Apr. 14, 2021.

(51) Int. Cl.
*G06T 19/00* (2011.01)
*A61B 34/00* (2016.01)
(Continued)

(52) U.S. Cl.
CPC .............. *G06T 11/00* (2013.01); *A61B 34/20* (2016.02); *A61B 34/25* (2016.02); *A61B 34/30* (2016.02);
(Continued)

(58) Field of Classification Search
None
See application file for complete search history.

(56) References Cited

U.S. PATENT DOCUMENTS 4,171,700 A 10/1979 Farin
4,849,752 A 7/1989 Bryant
(Continued)

FOREIGN PATENT DOCUMENTS

CA 3003058 A1 5/2017
CN 112603496 A 4/2021
(Continued)

OTHER PUBLICATIONS

Vávra et al., "Recent Development of Augmented Reality in Surgery: A Review", Journal of Healthcare Engineering, vol. 2017, Article ID 4574172, Aug. 21, 2017, pp. 1-9.
(Continued)

*Primary Examiner* — Joni Hsu
(74) *Attorney, Agent, or Firm* — Condo Roccia Koptiw LLP

(57) ABSTRACT

A surgical system is disclosed including an imaging device, a display configured to show a livestream of a surgical field of a surgical procedure, and a control system operably coupled to the imaging device and the display. The livestream is captured by the imaging device. The control system is configured to overlay, on the livestream, information associated with the surgical procedure, detect an occurrence of a triggering event, and adjust the overlaid information based on the occurrence of the triggering event.

18 Claims, 15 Drawing Sheets

(51) Int. Cl.

| | | |
|---|---|---|
| *A61B 34/20* | (2016.01) |
| *A61B 34/30* | (2016.01) |
| *A61B 34/32* | (2016.01) |
| *A61B 90/00* | (2016.01) |
| *G06F 3/14* | (2006.01) |
| *G06F 3/147* | (2006.01) |
| *G06T 7/00* | (2017.01) |
| *G06T 7/20* | (2017.01) |
| *G06T 11/00* | (2006.01) |
| *G06V 20/20* | (2022.01) |
| *G08B 21/18* | (2006.01) |
| *G16H 20/40* | (2018.01) |
| *G16H 40/67* | (2018.01) |
| *H04L 9/40* | (2022.01) |
| *H04L 67/12* | (2022.01) |
| *H04W 24/10* | (2009.01) |
| *H04W 76/14* | (2018.01) |
| *A61B 34/10* | (2016.01) |

(52) U.S. Cl.

CPC .............. *A61B 34/32* (2016.02); *A61B 34/76* (2016.02); *A61B 90/36* (2016.02); *A61B 90/361* (2016.02); *A61B 90/37* (2016.02); *A61B 90/39* (2016.02); *G06F 3/14* (2013.01); *G06F 3/1454* (2013.01); *G06F 3/147* (2013.01); *G06T 7/0012* (2013.01); *G06T 7/20* (2013.01); *G06T 19/006* (2013.01); *G06V 20/20* (2022.01); *G08B 21/182* (2013.01); *G16H 20/40* (2018.01); *G16H 40/67* (2018.01); *H04L 63/105* (2013.01); *H04L 67/12* (2013.01); *H04W 24/10* (2013.01); *H04W 76/14* (2018.02); *A61B 2034/102* (2016.02); *A61B 2034/2055* (2016.02); *A61B 2034/2072* (2016.02); *A61B 2034/252* (2016.02); *A61B 2034/254* (2016.02); *A61B 2090/365* (2016.02); *A61B 2090/368* (2016.02); *A61B 2090/371* (2016.02); *A61B 2090/372* (2016.02); *A61B 2090/373* (2016.02); *A61B 2090/3937* (2016.02); *A61B 2090/3975* (2016.02); *G06T 2207/10028* (2013.01); *G06T 2207/30024* (2013.01); *G06T 2210/41* (2013.01)

(56) References Cited

U.S. PATENT DOCUMENTS

| | | | |
|---|---|---|---|
| D303,787 | S | 10/1989 | Messenger et al. |
| D327,061 | S | 6/1992 | Soren et al. |
| 5,189,277 | A | 2/1993 | Boisvert et al. |
| 5,204,669 | A | 4/1993 | Dorfe et al. |
| 5,318,563 | A | 6/1994 | Malis et al. |
| 5,325,270 | A | 6/1994 | Wenger et al. |
| 5,425,375 | A | 6/1995 | Chin et al. |
| D379,346 | S | 5/1997 | Mieki |
| 5,690,504 | A | 11/1997 | Scanlan et al. |
| 5,693,042 | A | 12/1997 | Boiarski et al. |
| 5,724,468 | A | 3/1998 | Leone et al. |
| 6,049,467 | A | 4/2000 | Tamarkin et al. |
| 6,055,458 | A | 4/2000 | Cochran et al. |
| D431,811 | S | 10/2000 | Nishio et al. |
| 6,179,136 | B1 | 1/2001 | Kluge et al. |
| 6,269,411 | B1 | 7/2001 | Reasoner |
| 6,288,606 | B1 | 9/2001 | Ekman et al. |
| 6,416,471 | B1 | 7/2002 | Kumar et al. |
| 6,501,485 | B1 | 12/2002 | Dash et al. |
| 6,546,270 | B1 | 4/2003 | Goldin et al. |
| 6,584,358 | B2 | 6/2003 | Carter et al. |
| 6,611,793 | B1 | 8/2003 | Burnside et al. |
| 6,731,514 | B2 | 5/2004 | Evans |

| | | | | |
|---|---|---|---|---|
| 6,760,218 | B2 | 7/2004 | Fan | |
| 6,839,238 | B2 | 1/2005 | Derr et al. | |
| 6,843,657 | B2 | 1/2005 | Driscoll et al. | |
| 6,913,471 | B2 | 7/2005 | Smith | |
| 7,009,511 | B2 | 3/2006 | Mazar et al. | |
| 7,044,949 | B2 | 5/2006 | Orszulak et al. | |
| 7,074,205 | B1 | 7/2006 | Duffy et al. | |
| 7,134,994 | B2 | 11/2006 | Alpert et al. | |
| 7,171,784 | B2 | 2/2007 | Eenigenburg | |
| 7,217,269 | B2 | 5/2007 | El-Galley et al. | |
| 7,252,664 | B2 | 8/2007 | Nasab et al. | |
| 7,331,699 | B2 | 2/2008 | Gawalkiewicz et al. | |
| 7,344,532 | B2 | 3/2008 | Goble et al. | |
| 7,353,068 | B2 | 4/2008 | Tanaka et al. | |
| 7,408,439 | B2 | 8/2008 | Wang et al. | |
| D579,876 | S | 11/2008 | Novotney et al. | |
| D583,328 | S | 12/2008 | Chiang | |
| 7,496,418 | B2 | 2/2009 | Kim et al. | |
| D589,447 | S | 3/2009 | Sasada et al. | |
| 7,500,747 | B2 | 3/2009 | Howell et al. | |
| 7,518,502 | B2 | 4/2009 | Austin et al. | |
| 7,563,259 | B2 | 7/2009 | Takahashi | |
| 7,601,149 | B2 | 10/2009 | DiCarlo et al. | |
| 7,637,907 | B2 | 12/2009 | Blaha | |
| 7,656,671 | B2 | 2/2010 | Liu et al. | |
| 7,757,028 | B2 | 7/2010 | Druke et al. | |
| D631,252 | S | 1/2011 | Leslie | |
| 7,932,826 | B2 | 4/2011 | Fritchie et al. | |
| 7,945,065 | B2 | 5/2011 | Menzl et al. | |
| 7,945,342 | B2 | 5/2011 | Tsai et al. | |
| 7,982,776 | B2 | 7/2011 | Dunki-Jacobs et al. | |
| 7,995,045 | B2 | 8/2011 | Dunki-Jacobs | |
| 8,019,094 | B2 | 9/2011 | Hsieh et al. | |
| 8,086,008 | B2 | 12/2011 | Coste-maniere et al. | |
| D655,678 | S | 3/2012 | Kobayashi et al. | |
| D657,368 | S | 4/2012 | Magee et al. | |
| 8,239,066 | B2 | 8/2012 | Jennings et al. | |
| D667,838 | S | 9/2012 | Magee et al. | |
| D675,164 | S | 1/2013 | Kobayashi et al. | |
| D676,392 | S | 2/2013 | Gassauer | |
| D678,196 | S | 3/2013 | Miyauchi et al. | |
| D678,304 | S | 3/2013 | Yakoub et al. | |
| 8,423,182 | B2 | 4/2013 | Robinson et al. | |
| D687,146 | S | 7/2013 | Juzkiw et al. | |
| 8,504,136 | B1 | 8/2013 | Sun et al. | |
| 8,540,709 | B2 | 9/2013 | Allen | |
| 8,567,393 | B2 | 10/2013 | Hickle et al. | |
| D704,839 | S | 5/2014 | Juzkiw et al. | |
| 8,795,001 | B1 | 8/2014 | Lam et al. | |
| 8,819,581 | B2 | 8/2014 | Nakamura et al. | |
| D716,333 | S | 10/2014 | Chotin et al. | |
| 8,917,513 | B1 | 12/2014 | Hazzard | |
| 8,920,186 | B2 | 12/2014 | Shishikura | |
| 8,923,012 | B2 | 12/2014 | Kaufman et al. | |
| 8,968,296 | B2 | 3/2015 | McPherson | |
| 8,986,288 | B2 | 3/2015 | Konishi | |
| 9,017,326 | B2 | 4/2015 | Dinardo et al. | |
| D729,267 | S | 5/2015 | Yoo et al. | |
| 9,055,870 | B2 | 6/2015 | Meador et al. | |
| 9,065,394 | B2 | 6/2015 | Lim et al. | |
| 9,129,054 | B2 | 9/2015 | Nawana et al. | |
| 9,160,853 | B1 | 10/2015 | Daddi et al. | |
| 9,168,054 | B2 | 10/2015 | Turner et al. | |
| 9,168,085 | B2 * | 10/2015 | Juzkiw ................. A61B 18/14 |
| 9,168,091 | B2 | 10/2015 | Janssen et al. | |
| 9,198,711 | B2 | 12/2015 | Joseph | |
| 9,220,570 | B2 | 12/2015 | Kim et al. | |
| 9,226,766 | B2 | 1/2016 | Aldridge et al. | |
| 9,226,791 | B2 | 1/2016 | McCarthy et al. | |
| 9,237,921 | B2 | 1/2016 | Messerly et al. | |
| 9,265,429 | B2 | 2/2016 | St. Pierre et al. | |
| 9,277,961 | B2 | 3/2016 | Panescu et al. | |
| 9,277,969 | B2 | 3/2016 | Brannan et al. | |
| 9,281,615 | B1 | 3/2016 | Plaza et al. | |
| 9,320,646 | B2 | 4/2016 | Todd et al. | |
| 9,345,481 | B2 | 5/2016 | Hall et al. | |
| 9,345,900 | B2 | 5/2016 | Wu et al. | |
| 9,351,653 | B1 | 5/2016 | Harrison | |
| 9,427,255 | B2 | 8/2016 | Griffith et al. | |

(56) References Cited

U.S. PATENT DOCUMENTS

| | | | |
|---|---|---|---|
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,491,895 B2 | 11/2016 | Steeves et al. |
| 9,503,681 B1 | 11/2016 | Popescu et al. |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,629,176 B2 | 4/2017 | Guo et al. |
| 9,666,974 B2 | 5/2017 | Bopp |
| 9,713,503 B2 | 7/2017 | Goldschmidt |
| 9,715,271 B2 | 7/2017 | Kaestner |
| 9,750,563 B2 | 9/2017 | Shikhman et al. |
| 9,770,103 B2 | 9/2017 | Cochran et al. |
| 9,773,093 B2 | 9/2017 | Bernini et al. |
| 9,782,214 B2 | 10/2017 | Houser et al. |
| 9,788,907 B1 | 10/2017 | Alvi et al. |
| 9,804,977 B2 | 10/2017 | Ghosh et al. |
| 9,867,670 B2 | 1/2018 | Brannan et al. |
| 9,892,564 B1 | 2/2018 | Cvetko et al. |
| 9,907,196 B2 | 2/2018 | Susini et al. |
| 9,935,794 B1 | 4/2018 | Cao et al. |
| 9,971,395 B2 | 5/2018 | Chenault et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| D832,211 S | 10/2018 | Ladd et al. |
| 10,098,527 B2 | 10/2018 | Weisenburgh, II et al. |
| 10,105,470 B2 | 10/2018 | Reasoner et al. |
| 10,109,835 B2 | 10/2018 | Yang |
| D834,541 S | 11/2018 | You et al. |
| 10,117,702 B2 | 11/2018 | Danziger et al. |
| 10,128,612 B1 | 11/2018 | Casto |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,019 B2 | 1/2019 | Nawana et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,262,453 B2 | 4/2019 | Mountney et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,441,345 B2 | 10/2019 | Aldridge et al. |
| 10,449,004 B2 | 10/2019 | Ferro et al. |
| 10,475,244 B2 | 11/2019 | Cvetko et al. |
| 10,493,287 B2 | 12/2019 | Yoder et al. |
| 10,499,847 B2 | 12/2019 | Latimer et al. |
| 10,499,996 B2 | 12/2019 | de Almeida Barreto |
| 10,523,122 B2 | 12/2019 | Han et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,610,310 B2 | 4/2020 | Todd et al. |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,729,502 B1 | 8/2020 | Wolf et al. |
| 10,743,872 B2 | 8/2020 | Leimbach et al. |
| 10,758,309 B1 | 9/2020 | Chow et al. |
| 10,758,310 B2 | 9/2020 | Shelton, IV et al. |
| 10,772,673 B2 | 9/2020 | Allen, IV et al. |
| 10,878,966 B2 | 12/2020 | Wolf et al. |
| 10,881,399 B2 | 1/2021 | Shelton, IV et al. |
| 10,898,256 B2 | 1/2021 | Yates et al. |
| 10,925,598 B2 | 2/2021 | Scheib et al. |
| 10,932,705 B2 | 3/2021 | Muhsin et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| 10,989,724 B1 | 4/2021 | Holmes et al. |
| 11,000,270 B2 | 5/2021 | Scheib et al. |
| 11,006,100 B1 | 5/2021 | Douglas |
| D924,139 S | 7/2021 | Jayme |
| 11,056,244 B2 | 7/2021 | Shelton, IV et al. |
| 11,058,497 B2 | 7/2021 | Altmann et al. |
| 11,065,079 B2 | 7/2021 | Wolf et al. |
| 11,071,595 B2 | 7/2021 | Johnson et al. |
| D928,725 S | 8/2021 | Oberkircher et al. |
| D928,726 S | 8/2021 | Asher et al. |
| 11,083,489 B2 | 8/2021 | Fujii et al. |
| 11,114,199 B2 | 9/2021 | Moctezuma De La Barrera |
| 11,116,587 B2 | 9/2021 | Wolf et al. |
| D939,545 S | 12/2021 | Oberkircher et al. |
| 11,218,822 B2 | 1/2022 | Morgan et al. |
| 11,259,793 B2 | 3/2022 | Scheib et al. |
| 11,259,875 B2 | 3/2022 | Boutin et al. |
| 11,272,839 B2 | 3/2022 | Al-Ali et al. |
| 11,284,963 B2 | 3/2022 | Shelton, IV et al. |
| 11,296,540 B2 | 4/2022 | Kirleis et al. |
| 11,298,128 B2 | 4/2022 | Messerly et al. |
| 11,304,763 B2 | 4/2022 | Shelton, IV et al. |
| 11,314,846 B1 | 4/2022 | Colin et al. |
| 11,341,726 B2 | 5/2022 | Tsuda et al. |
| 11,350,978 B2 | 6/2022 | Henderson et al. |
| 11,369,366 B2 | 6/2022 | Scheib et al. |
| 11,382,699 B2 | 7/2022 | Wassall et al. |
| 11,382,700 B2 | 7/2022 | Calloway et al. |
| 11,419,604 B2 | 8/2022 | Scheib et al. |
| 11,424,027 B2 | 8/2022 | Shelton, IV |
| 11,432,877 B2 | 9/2022 | Nash et al. |
| 11,464,581 B2 | 10/2022 | Calloway |
| 11,471,206 B2 | 10/2022 | Henderson et al. |
| 11,478,820 B2 | 10/2022 | Bales, Jr. et al. |
| 11,504,192 B2 | 11/2022 | Shelton, IV et al. |
| 11,510,720 B2 | 11/2022 | Morgan et al. |
| 11,510,750 B2 | 11/2022 | Dulin et al. |
| 11,823,374 B2 | 11/2023 | Schneider et al. |
| 11,836,863 B2 | 12/2023 | Flexman et al. |
| 12,349,861 B2 | 7/2025 | Charles et al. |
| 2001/0029315 A1 | 10/2001 | Sakurai et al. |
| 2003/0078631 A1 | 4/2003 | Nelson et al. |
| 2003/0199794 A1 | 10/2003 | Sakurai et al. |
| 2003/0199864 A1 | 10/2003 | Eick |
| 2004/0030328 A1 | 2/2004 | Eggers et al. |
| 2004/0059323 A1 | 3/2004 | Sturm et al. |
| 2004/0111045 A1 | 6/2004 | Sullivan et al. |
| 2004/0164983 A1 | 8/2004 | Khozai |
| 2005/0010209 A1 | 1/2005 | Lee et al. |
| 2005/0013459 A1 | 1/2005 | Maekawa |
| 2005/0113823 A1 | 5/2005 | Reschke et al. |
| 2005/0165390 A1 | 7/2005 | Mauti et al. |
| 2005/0229110 A1 | 10/2005 | Gegner et al. |
| 2005/0251233 A1 | 11/2005 | Kanzius |
| 2006/0082542 A1 | 4/2006 | Morita et al. |
| 2006/0085049 A1 | 4/2006 | Cory et al. |
| 2006/0136622 A1 | 6/2006 | Rouvelin et al. |
| 2006/0149418 A1 | 7/2006 | Anvari |
| 2006/0256516 A1 | 11/2006 | Cho |
| 2007/0076363 A1 | 4/2007 | Liang et al. |
| 2007/0211930 A1 | 9/2007 | Dolwick et al. |
| 2007/0282321 A1 | 12/2007 | Shah et al. |
| 2008/0072896 A1 | 3/2008 | Setzer et al. |
| 2008/0129465 A1 | 6/2008 | Rao |
| 2008/0249377 A1 | 10/2008 | Molducci et al. |
| 2008/0316304 A1 | 12/2008 | Claus et al. |
| 2009/0036884 A1 | 2/2009 | Gregg et al. |
| 2009/0131929 A1 | 5/2009 | Shimizu |
| 2009/0192524 A1 | 7/2009 | Itkowitz et al. |
| 2009/0216091 A1 | 8/2009 | Arndt |
| 2009/0234352 A1 | 9/2009 | Behnke et al. |
| 2010/0036405 A1 | 2/2010 | Giordano et al. |
| 2010/0042010 A1 | 2/2010 | Dekker et al. |
| 2010/0053213 A1 | 3/2010 | Ishida et al. |
| 2010/0069939 A1 | 3/2010 | Konishi |
| 2010/0076453 A1 | 3/2010 | Morris et al. |

(56) References Cited

U.S. PATENT DOCUMENTS

| | | | |
|---|---|---|---|
| 2010/0092006 A1 | 4/2010 | Rosen | |
| 2010/0120266 A1 | 5/2010 | Rimborg | |
| 2010/0198200 A1 | 8/2010 | Horvath | |
| 2010/0312239 A1 | 12/2010 | Sclig | |
| 2011/0105895 A1 | 5/2011 | Kornblau et al. | |
| 2011/0118748 A1 | 5/2011 | Itkowitz | |
| 2011/0125149 A1 | 5/2011 | El-Galley et al. | |
| 2011/0130689 A1 | 6/2011 | Cohen et al. | |
| 2011/0190588 A1* | 8/2011 | McKay | A61B 17/0206 |
| | | | 600/202 |
| 2011/0245630 A1 | 10/2011 | St. Pierre et al. | |
| 2011/0273465 A1 | 11/2011 | Konishi et al. | |
| 2011/0298814 A1 | 12/2011 | Mathew et al. | |
| 2011/0306840 A1 | 12/2011 | Allen et al. | |
| 2012/0029304 A1 | 2/2012 | Medina et al. | |
| 2012/0082036 A1 | 4/2012 | Abedi et al. | |
| 2012/0116380 A1 | 5/2012 | Madan et al. | |
| 2012/0132661 A1 | 5/2012 | Gu et al. | |
| 2013/0031201 A1 | 1/2013 | Kagan et al. | |
| 2013/0038707 A1 | 2/2013 | Cunningham et al. | |
| 2013/0176220 A1 | 7/2013 | Merschon et al. | |
| 2013/0197357 A1 | 8/2013 | Green et al. | |
| 2013/0197503 A1 | 8/2013 | Orszulak | |
| 2013/0267975 A1 | 10/2013 | Timm et al. | |
| 2013/0268283 A1 | 10/2013 | Vann et al. | |
| 2013/0303851 A1 | 11/2013 | Griffith et al. | |
| 2013/0321159 A1 | 12/2013 | Schofield et al. | |
| 2014/0009894 A1 | 1/2014 | Yu | |
| 2014/0052150 A1 | 2/2014 | Taylor et al. | |
| 2014/0058714 A1 | 2/2014 | Boyer | |
| 2014/0087573 A1 | 3/2014 | Kroeckel | |
| 2014/0155721 A1 | 6/2014 | Hauck et al. | |
| 2014/0179997 A1 | 6/2014 | Grunberg et al. | |
| 2014/0194683 A1 | 7/2014 | Nakaguchi | |
| 2014/0221740 A1 | 8/2014 | Kawula et al. | |
| 2014/0226572 A1 | 8/2014 | Thota et al. | |
| 2014/0262598 A1 | 9/2014 | Miki et al. | |
| 2014/0263552 A1 | 9/2014 | Hall et al. | |
| 2014/0343358 A1 | 11/2014 | Hameed et al. | |
| 2015/0019259 A1 | 1/2015 | Qureshi et al. | |
| 2015/0057575 A1 | 2/2015 | Tsusaka et al. | |
| 2015/0070388 A1 | 3/2015 | Sheaffer et al. | |
| 2015/0190189 A1 | 7/2015 | Yates et al. | |
| 2015/0265369 A1 | 9/2015 | Garbey et al. | |
| 2015/0272575 A1 | 10/2015 | Leimbach et al. | |
| 2015/0289929 A1 | 10/2015 | Toth et al. | |
| 2016/0045247 A1 | 2/2016 | Heim et al. | |
| 2016/0058286 A1 | 3/2016 | Joshua et al. | |
| 2016/0066184 A1 | 3/2016 | Bhargav-Spantzel et al. | |
| 2016/0074096 A1 | 3/2016 | Lieu | |
| 2016/0120591 A1 | 5/2016 | Smith et al. | |
| 2016/0174897 A1 | 6/2016 | Sherman | |
| 2016/0225192 A1 | 8/2016 | Jones et al. | |
| 2016/0287312 A1 | 10/2016 | Tegg et al. | |
| 2016/0287337 A1 | 10/2016 | Aram et al. | |
| 2017/0000553 A1 | 1/2017 | Wiener et al. | |
| 2017/0090507 A1 | 3/2017 | Wiener et al. | |
| 2017/0189096 A1 | 7/2017 | Danziger et al. | |
| 2017/0202595 A1 | 7/2017 | Shelton, IV | |
| 2017/0209225 A1 | 7/2017 | Wu | |
| 2017/0251305 A1 | 8/2017 | Fathollahi | |
| 2017/0252091 A1 | 9/2017 | Honda | |
| 2017/0258526 A1 | 9/2017 | Lang | |
| 2017/0296036 A1 | 10/2017 | Newman | |
| 2017/0296213 A1 | 10/2017 | Swensgard et al. | |
| 2017/0319259 A1 | 11/2017 | Dunning | |
| 2017/0333275 A1 | 11/2017 | Itkowitz et al. | |
| 2017/0360466 A1 | 12/2017 | Brown et al. | |
| 2017/0367766 A1 | 12/2017 | Mahfouz | |
| 2018/0014872 A1 | 1/2018 | Dickerson | |
| 2018/0032130 A1 | 2/2018 | Meglan | |
| 2018/0042659 A1 | 2/2018 | Rupp et al. | |
| 2018/0043037 A1 | 2/2018 | Dalma-Weiszhausz et al. | |
| 2018/0049795 A1 | 2/2018 | Swayze et al. | |
| 2018/0065248 A1 | 3/2018 | Barral et al. | |
| 2018/0078216 A1 | 3/2018 | Baker et al. | |
| 2018/0082480 A1* | 3/2018 | White | A61B 90/94 |
| 2018/0092699 A1 | 4/2018 | Finley | |
| 2018/0099161 A1 | 4/2018 | Honda | |
| 2018/0168741 A1 | 6/2018 | Swayze et al. | |
| 2018/0173323 A1 | 6/2018 | Harvey et al. | |
| 2018/0221005 A1 | 8/2018 | Hamel et al. | |
| 2018/0228528 A1 | 8/2018 | Fraasch et al. | |
| 2018/0228555 A1 | 8/2018 | Charron et al. | |
| 2018/0235441 A1 | 8/2018 | Huang et al. | |
| 2018/0243573 A1 | 8/2018 | Yoder et al. | |
| 2018/0262916 A1 | 9/2018 | Polley et al. | |
| 2018/0263557 A1 | 9/2018 | Kahlman | |
| 2018/0289338 A1 | 10/2018 | Meador et al. | |
| 2018/0317826 A1 | 11/2018 | Muhsin et al. | |
| 2018/0333207 A1 | 11/2018 | Moctezuma De La Barrera | |
| 2018/0368930 A1 | 12/2018 | Esterberg et al. | |
| 2019/0006047 A1 | 1/2019 | Gorek et al. | |
| 2019/0035153 A1 | 1/2019 | Dange | |
| 2019/0038362 A1 | 2/2019 | Nash et al. | |
| 2019/0069957 A1 | 3/2019 | Barral et al. | |
| 2019/0104919 A1 | 4/2019 | Shelton, IV et al. | |
| 2019/0117326 A1 | 4/2019 | Wada | |
| 2019/0125361 A1 | 5/2019 | Shelton et al. | |
| 2019/0125451 A1* | 5/2019 | Srimohanarajah | G16H 30/40 |
| 2019/0125454 A1* | 5/2019 | Stokes | A61B 18/1206 |
| 2019/0125455 A1 | 5/2019 | Shelton, IV et al. | |
| 2019/0125459 A1 | 5/2019 | Shelton et al. | |
| 2019/0183576 A1 | 6/2019 | Fahim et al. | |
| 2019/0183591 A1 | 6/2019 | Johnson et al. | |
| 2019/0200844 A1 | 7/2019 | Shelton, IV et al. | |
| 2019/0200906 A1 | 7/2019 | Shelton, IV et al. | |
| 2019/0200981 A1 | 7/2019 | Harris et al. | |
| 2019/0200987 A1 | 7/2019 | Shelton, IV et al. | |
| 2019/0201046 A1 | 7/2019 | Shelton, IV et al. | |
| 2019/0201102 A1 | 7/2019 | Shelton, IV et al. | |
| 2019/0201114 A1 | 7/2019 | Shelton et al. | |
| 2019/0201116 A1 | 7/2019 | Shelton, IV et al. | |
| 2019/0201117 A1 | 7/2019 | Yates et al. | |
| 2019/0201127 A1 | 7/2019 | Shelton, IV et al. | |
| 2019/0201136 A1 | 7/2019 | Shelton, IV et al. | |
| 2019/0201137 A1 | 7/2019 | Shelton, IV et al. | |
| 2019/0201140 A1 | 7/2019 | Yates et al. | |
| 2019/0201158 A1 | 7/2019 | Shelton, IV et al. | |
| 2019/0205001 A1 | 7/2019 | Messerly et al. | |
| 2019/0206004 A1 | 7/2019 | Shelton, IV et al. | |
| 2019/0206562 A1 | 7/2019 | Shelton, IV et al. | |
| 2019/0206563 A1 | 7/2019 | Shelton, IV et al. | |
| 2019/0206565 A1 | 7/2019 | Shelton, IV | |
| 2019/0206569 A1 | 7/2019 | Shelton et al. | |
| 2019/0224434 A1 | 7/2019 | Silver et al. | |
| 2019/0236840 A1 | 8/2019 | Zuckerman et al. | |
| 2019/0247141 A1 | 8/2019 | Batchelor et al. | |
| 2019/0278262 A1 | 9/2019 | Taylor et al. | |
| 2019/0279524 A1 | 9/2019 | Stoyanov et al. | |
| 2019/0282307 A1 | 9/2019 | Azizian et al. | |
| 2019/0290297 A1 | 9/2019 | Haider et al. | |
| 2019/0348169 A1 | 11/2019 | Gibby et al. | |
| 2019/0371012 A1 | 12/2019 | Flexman et al. | |
| 2020/0004487 A1 | 1/2020 | Hanajima et al. | |
| 2020/0015895 A1 | 1/2020 | Frielinghaus et al. | |
| 2020/0015898 A1 | 1/2020 | Scheib et al. | |
| 2020/0015899 A1 | 1/2020 | Scheib et al. | |
| 2020/0015900 A1 | 1/2020 | Scheib et al. | |
| 2020/0015902 A1 | 1/2020 | Scheib et al. | |
| 2020/0015906 A1 | 1/2020 | Scheib et al. | |
| 2020/0015907 A1 | 1/2020 | Scheib | |
| 2020/0015914 A1 | 1/2020 | Scheib et al. | |
| 2020/0015924 A1 | 1/2020 | Scheib et al. | |
| 2020/0038120 A1 | 2/2020 | Ziraknejad et al. | |
| 2020/0078070 A1 | 3/2020 | Henderson et al. | |
| 2020/0078071 A1 | 3/2020 | Asher | |
| 2020/0078076 A1 | 3/2020 | Henderson et al. | |
| 2020/0078078 A1 | 3/2020 | Henderson et al. | |
| 2020/0078080 A1 | 3/2020 | Henderson et al. | |
| 2020/0078081 A1 | 3/2020 | Jayme et al. | |
| 2020/0078082 A1 | 3/2020 | Henderson et al. | |
| 2020/0078083 A1 | 3/2020 | Sprinkle et al. | |
| 2020/0078089 A1 | 3/2020 | Henderson et al. | |

(56) References Cited

U.S. PATENT DOCUMENTS

| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0093357 A1 | 3/2020 | Scott et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0159313 A1 | 5/2020 | Gibby et al. |
| 2020/0237031 A1 | 7/2020 | Daniels et al. |
| 2020/0237452 A1 | 7/2020 | Wolf et al. |
| 2020/0246084 A1 | 8/2020 | Azizian |
| 2020/0268469 A1 | 8/2020 | Wolf et al. |
| 2020/0268472 A1 | 8/2020 | Wolf et al. |
| 2020/0305924 A1 | 10/2020 | Carroll |
| 2020/0305945 A1 | 10/2020 | Morgan et al. |
| 2020/0315707 A1 | 10/2020 | Venkataraman |
| 2020/0315734 A1 | 10/2020 | El Amm |
| 2020/0322516 A1 | 10/2020 | Doser et al. |
| 2020/0342228 A1 | 10/2020 | Prevrhal et al. |
| 2020/0359892 A1 | 11/2020 | Rollins et al. |
| 2020/0384287 A1* | 12/2020 | Hetz .................... A61N 5/0613 |
| 2020/0405529 A1* | 12/2020 | Taylor ...................... G08B 3/10 |
| 2021/0000564 A1 | 1/2021 | Amanatullah et al. |
| 2021/0015343 A1 | 1/2021 | Uyama et al. |
| 2021/0093390 A1 | 4/2021 | Poltaretskyi et al. |
| 2021/0121246 A1 | 4/2021 | Gudalo |
| 2021/0128254 A1 | 5/2021 | Geric et al. |
| 2021/0158779 A1 | 5/2021 | Singh |
| 2021/0169578 A1 | 6/2021 | Calloway et al. |
| 2021/0169581 A1 | 6/2021 | Calloway et al. |
| 2021/0174956 A1 | 6/2021 | Mcginley et al. |
| 2021/0192759 A1 | 6/2021 | Lang |
| 2021/0193681 A1 | 6/2021 | Baek |
| 2021/0196381 A1 | 7/2021 | Eckert et al. |
| 2021/0196383 A1 | 7/2021 | Shelton, IV et al. |
| 2021/0196425 A1 | 7/2021 | Shelton et al. |
| 2021/0203889 A1 | 7/2021 | Fung et al. |
| 2021/0205020 A1 | 7/2021 | Shelton, IV et al. |
| 2021/0212717 A1 | 7/2021 | Yates et al. |
| 2021/0236755 A1 | 8/2021 | King et al. |
| 2021/0259789 A1 | 8/2021 | Wright et al. |
| 2021/0264680 A1 | 8/2021 | Cvetko et al. |
| 2021/0267664 A1 | 9/2021 | Lennartz et al. |
| 2021/0306691 A1 | 9/2021 | Thomas et al. |
| 2021/0307861 A1 | 10/2021 | Hufford et al. |
| 2021/0313052 A1 | 10/2021 | Makrinich et al. |
| 2021/0333864 A1 | 10/2021 | Harvey et al. |
| 2021/0346092 A1* | 11/2021 | Redmond ............... A61B 34/25 |
| 2021/0369394 A1 | 12/2021 | Braido et al. |
| 2021/0385889 A1 | 12/2021 | Patel |
| 2022/0032442 A1 | 2/2022 | Sheffield et al. |
| 2022/0104896 A1 | 4/2022 | Shelton, IV et al. |
| 2022/0104897 A1 | 4/2022 | Shelton, IV et al. |
| 2022/0104911 A1 | 4/2022 | Shelton, IV et al. |
| 2022/0104912 A1 | 4/2022 | Shelton, IV et al. |
| 2022/0142573 A1 | 5/2022 | Li et al. |
| 2022/0151704 A1 | 5/2022 | Nikou |
| 2022/0155910 A1 | 5/2022 | Jeong |
| 2022/0160428 A1* | 5/2022 | Murray ............... A61B 17/7086 |
| 2022/0188545 A1 | 6/2022 | Nagar et al. |
| 2022/0237878 A1 | 7/2022 | Tartz et al. |
| 2022/0257333 A1 | 8/2022 | Haider |
| 2022/0261056 A1 | 8/2022 | Motoi et al. |
| 2022/0283631 A1* | 9/2022 | Peng ...................... G06V 20/20 |
| 2022/0287676 A1 | 9/2022 | Steines et al. |
| 2022/0313338 A1 | 10/2022 | Carroll et al. |
| 2022/0313341 A1 | 10/2022 | Wiener et al. |
| 2022/0313342 A1 | 10/2022 | Leuck et al. |
| 2022/0313357 A1 | 10/2022 | Geresy et al. |
| 2022/0313369 A1 | 10/2022 | Oberkircher et al. |
| 2022/0313370 A1 | 10/2022 | Morgan et al. |
| 2022/0313371 A1 | 10/2022 | Morgan et al. |
| 2022/0313372 A1 | 10/2022 | Herman et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2022/0319693 A1 | 10/2022 | Oberkircher et al. |
| 2022/0321059 A1 | 10/2022 | Samuel et al. |
| 2022/0322523 A1 | 10/2022 | Jayme et al. |
| 2022/0331013 A1 | 10/2022 | Shelton, IV et al. |
| 2022/0331047 A1 | 10/2022 | Shelton, IV et al. |
| 2022/0331048 A1 | 10/2022 | Shelton, IV et al. |
| 2022/0331049 A1 | 10/2022 | Shelton, IV et al. |
| 2022/0331050 A1 | 10/2022 | Shelton, IV et al. |
| 2022/0331051 A1 | 10/2022 | Shelton, IV et al. |
| 2022/0331052 A1 | 10/2022 | Shelton, IV et al. |
| 2022/0331053 A1 | 10/2022 | Kimball et al. |
| 2022/0331054 A1 | 10/2022 | Kimball et al. |
| 2022/0331056 A1 | 10/2022 | Shelton, IV et al. |
| 2022/0334787 A1 | 10/2022 | Jogan et al. |
| 2022/0335604 A1 | 10/2022 | Vanosdoll et al. |
| 2022/0335660 A1 | 10/2022 | Shelton, IV et al. |
| 2022/0335696 A1 | 10/2022 | Shelton, IV et al. |
| 2022/0336078 A1 | 10/2022 | Wise et al. |
| 2022/0336097 A1 | 10/2022 | Shelton, IV et al. |
| 2022/0337891 A1 | 10/2022 | Burnley et al. |
| 2022/0338049 A1 | 10/2022 | Ross et al. |
| 2022/0387128 A1 | 12/2022 | Bail et al. |
| 2023/0038130 A1 | 2/2023 | Cvetko et al. |
| 2023/0061534 A1 | 3/2023 | Stopek |
| 2023/0071306 A1 | 3/2023 | Miller et al. |
| 2023/0072423 A1 | 3/2023 | Osborn et al. |
| 2023/0121709 A1 | 4/2023 | Xu et al. |
| 2023/0157757 A1 | 5/2023 | Braido et al. |
| 2023/0157762 A1 | 5/2023 | Braido et al. |
| 2024/0130795 A1* | 4/2024 | Clayton ................. A61B 34/10 |
| 2024/0138931 A1* | 5/2024 | Lefauconnier ..... A61B 17/7011 |
| 2024/0176441 A1 | 5/2024 | Yang et al. |
| 2024/0325085 A1 | 10/2024 | Ryan et al. |

FOREIGN PATENT DOCUMENTS

| EP | 0408160 A1 | 1/1991 |
| EP | 0473987 A1 | 3/1992 |
| EP | 0929263 B1 | 7/1999 |
| EP | 1006892 B1 | 6/2009 |
| EP | 2942023 A2 | 11/2015 |
| EP | 3053279 A1 | 8/2016 |
| EP | 3387982 A1 | 10/2018 |
| JP | 2000-271145 A | 10/2000 |
| JP | 2001029353 A | 2/2001 |
| JP | 2006-149560 A | 6/2006 |
| JP | 2007-007041 A | 1/2007 |
| JP | 2007-029232 A | 2/2007 |
| JP | 2021-045341 A | 3/2021 |
| WO | WO-0112089 A1 | 2/2001 |
| WO | WO-2008053485 A1 | 5/2008 |
| WO | 2014/010177 A1 | 1/2014 |
| WO | WO-2014031800 A1 | 2/2014 |
| WO | WO-2014071184 A1 | 5/2014 |
| WO | WO-2015047693 A1 | 4/2015 |
| WO | 2016/013636 A1 | 1/2016 |
| WO | 2016154557 A1 | 9/2016 |
| WO | WO-2017058617 A2 | 4/2017 |
| WO | 2017/099153 A1 | 6/2017 |
| WO | 2017/221367 A1 | 12/2017 |
| WO | WO-2018116247 A1 | 6/2018 |
| WO | WO-2019215354 A1 | 11/2019 |
| WO | 2020112217 A1 | 6/2020 |
| WO | 2020180917 A1 | 9/2020 |

(56)     References Cited

FOREIGN PATENT DOCUMENTS

| WO | WO-2021044136 A1 | 3/2021 |
| WO | 2021/146313 A1 | 7/2021 |

OTHER PUBLICATIONS

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.Mar. 2008, published Dec. 28, 2012.

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

Zhu et al. "Haptic-feedback smart glove as a creative human-machine interface (HMI) for virtual/augmented reality applications," Sci. Adv, vol. 6, No. 19, May 8, 2020.

Qian, et al., "A Review of Augmented Reality in Robotic-Assisted Surgery", IEEE Transactions on Medical Robotics and Bionics, IEEE, vol. 2, No. 1, pp. 1-16, Feb. 2020.

Yu et al., "Skin-Integrated Wireless Haptic Interfaces for Virtual and Augmented Reality," Nature, vol. 575, pp. 473-479, Nov. 21, 2019.

Li et al., "Wearable Energy Harvesters Generating Electricity From Low-Frequency Human Limb Movement," Microsystems & Nanoengineering (2018), vol. 4(24), 13 pages.

"International Search Report and Written Opinion received for PCT Application No. PCT/IB2022/053360", Jul. 4, 2022, 12 pages.

"International Search Report and Written Opinion received for PCT Application No. PCT/IB2022/053362", Jul. 1, 2022, 13 pages.

"International Search Report and Written Opinion received for PCT Application No. PCT/IB2022/053363", Jun. 30, 2022, 14 pages.

"International Search Report and Written Opinion received for PCT Application No. PCT/IB2022/053364", Jul. 8, 2022, 11 pages.

"International Search Report and Written Opinion received for PCT Application No. PCT/IB2022/053365", Jul. 4, 2022, 16 pages.

"International Search Report and Written Opinion received for PCT Application No. PCT/IB2022/053369", Jul. 13, 2022, 12 pages.

"International Search Report and Written Opinion received for PCT Application No. PCT/IB2022/053370", Jul. 15, 2022, 14 pages.

"International Search Report and Written Opinion received for PCT Application No. PCT/IB2022/053371", Jul. 5, 2022, 12 pages.

"International Search Report and Written Opinion received for PCT Application No. PCT/IB2022/053377", Jun. 22, 2022, 12 pages.

"International Search Report and Written Opinion received for PCT Application No. PCT/IB2022/053378", Jul. 7, 2022, 13 pages.

"Invitation to Pay Additional Fees received for PCT Application No. PCT/IB2022/053375", Jul. 15, 2022, 11 pages.

International Search Report and Written Opinion received for PCT Application No. PCT/IB2022/053375 mailed on Oct. 4, 2022, 22 pages.

Kaushik et al., "Emerging Thermal Technology Enabled Augmented Reality", Advanced Functional Materials, vol. 31, No. 39, Feb. 17, 2021., pp. 1-27.

Zherdeva, et al., "Virtual Scalpel Simulation In The VR and AR Environments", Proceedings Of SPIE, vol. 11310, Feb. 19, 2020, 7 pages.

* cited by examiner

5200

| WHAT THE HUB KNOWS | TYPE OF DATA | PROCEDURE STEP |
|---|---|---|
| THORACIC PROCEDURE | SELECT PATIENT DATA (5202) | PULL ELECTRONIC MEDICAL RECORDS |
| NOT A WEDGE PROCEDURE | SCAN PRODUCTS (5204) | SCAN INCOMING SUPPLIES |
| CONFIRM PATIENT | UNIQUE ID (5206) | SCAN PATIENT BAND |
| VATS | SMOKE EVAC. DATA INSUFFLATION DATA SCOPE DATA (5208) | TURN ON HUB AUXILIARY EQUIPMENT |
| CONFIRM PATIENT IS IN O.R. | EKG DATA (5210) | ATTACH EKG |
| PATIENT UNDER | EKG, BP AND VENTILATOR DATA (5212) | INDUCE ANESTHESIA |
| PROCEDURE BEGINS | VENTILATOR DATA (5214) | COLLAPSE LUNG |
| CONFIRM LOBECTOMY vs. SEGMENTECTOMY LAP PORTION STARTS | SCOPE DATA (5216) | SCOPE IMAGE |

| WHAT THE HUB KNOWS | TYPE OF DATA | PROCEDURE STEP |
|---|---|---|
| DISSECT TO MOBILIZE LUNG | GENERATOR DATA (5218) | DISSECTION |
| LIGATE ARTERY & VEIN | STAPLER DATA (5220) | LIGATION |
| TRANSECT PARENCHYMA | STAPLER & CATRIDGE DATA (5222) | SEGMENTECTOMY |
| DISSECT NODES LEAK TEST | GENERATOR DATA (5224) | NODE DISSECTION |
| PATIENT EMERGENCE | VENTILATOR DATA (5226) | REVERSE ANESTHESIA |
| PATIENT TRANSFER TO RECOVERY ROOM | LOSS OF EKG DATA LOSS OF BP DATA (5228) | REMOVE MONITORS |

FIG. 11

SYSTEMS AND METHODS FOR CHANGING DISPLAY OVERLAY OF SURGICAL FIELD VIEW BASED ON TRIGGERING EVENTS

CROSS-REFERENCE TO RELATED APPLICATIONS

This application claims the benefit under 35 U.S.C. § 119(e) to U.S. Provisional Patent Application No. 63/174,674, titled HEADS UP DISPLAY, filed Apr. 14, 2021 and to U.S. Provisional Patent Application No. 63/284,326, titled INTRAOPERATIVE DISPLAY FOR SURGICAL SYSTEMS, filed Nov. 30, 2021, the disclosure of each of which is herein incorporated by reference in its entirety.

BACKGROUND

This disclosure relates to apparatuses, systems, and methods for providing an augmented reality interactive experience during a surgical procedure. During a surgical procedure it would be desirable to provide an augmented reality interactive experience of a real-world environment where objects that reside in the real world are enhanced by overlaying computer-generated perceptual information, sometimes across multiple sensory modalities, including visual, auditory, haptic, somatosensory, and olfactory. In the context of this disclosure, images of a surgical field and surgical instruments and other objects appearing in the surgical field are enhanced by overlaying computer-generated visual, auditory, haptic, somatosensory, olfactory, or other sensory information onto the real world images of the surgical field and instruments or other objects appearing in the surgical field. The images may be streamed in real time or may be still images.

Real world surgical instruments include a variety of surgical devices including energy, staplers, or combined energy and staplers. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices are surgical instruments used to cut and staple tissue in a variety of surgical procedures, including bariatric, thoracic, colorectal, gynecologic, urologic and general surgery.

SUMMARY

In various instances, this disclosure provides a surgical system including an imaging device, a display configured to show a livestream of a surgical field of a surgical procedure, and a control system operably coupled to the imaging device and the display. The livestream is captured by the imaging device. The control system is configured to overlay, on the livestream, information associated with the surgical procedure, detect an occurrence of a triggering event, and adjust the overlaid information based on the occurrence of the triggering event.

In various instances, this disclosure provides a surgical system including an imaging device, a display configured to show a livestream of a surgical field of a surgical procedure, and a control system operably coupled to the imaging device and the display. The livestream is captured by the imaging device. The control system is configured to overlay, on the livestream, information associated with the surgical procedure, set a triggering event count, detect partial triggering events, adjust the triggering event count based on an occurrence of a partial triggering event, and adjust the overlaid information based on the triggering event count reaching or exceeding a triggering event threshold.

In various instances, this disclosure provides a surgical system including an imaging device, a display configured to show a livestream of a surgical field of a surgical procedure, a situational awareness module, and a control system operably coupled to the imaging device, the display, and the situational awareness module. The livestream is captured by the imaging device. The control system is configured to overlay, on the livestream, information associated with the surgical procedure, determine, by the situational awareness module, a step of the surgical procedure, detect an occurrence of a triggering event, and adjust the overlaid information based on the occurrence of the triggering event and the step of the surgical procedure

FIGURES

The various aspects described herein, both as to organization and methods of operation, together with further objects and advantages thereof, may best be understood by reference to the following description, taken in conjunction with the accompanying drawings as follows.

FIG. 11 illustrates a timeline of a situational awareness surgical procedure, according to one aspect of this disclosure.

Corresponding reference characters indicate corresponding parts throughout the several views. The exemplifications set out herein illustrate various disclosed embodiments, in one form, and such exemplifications are not to be construed as limiting the scope thereof in any manner.

DESCRIPTION

Figure 1:
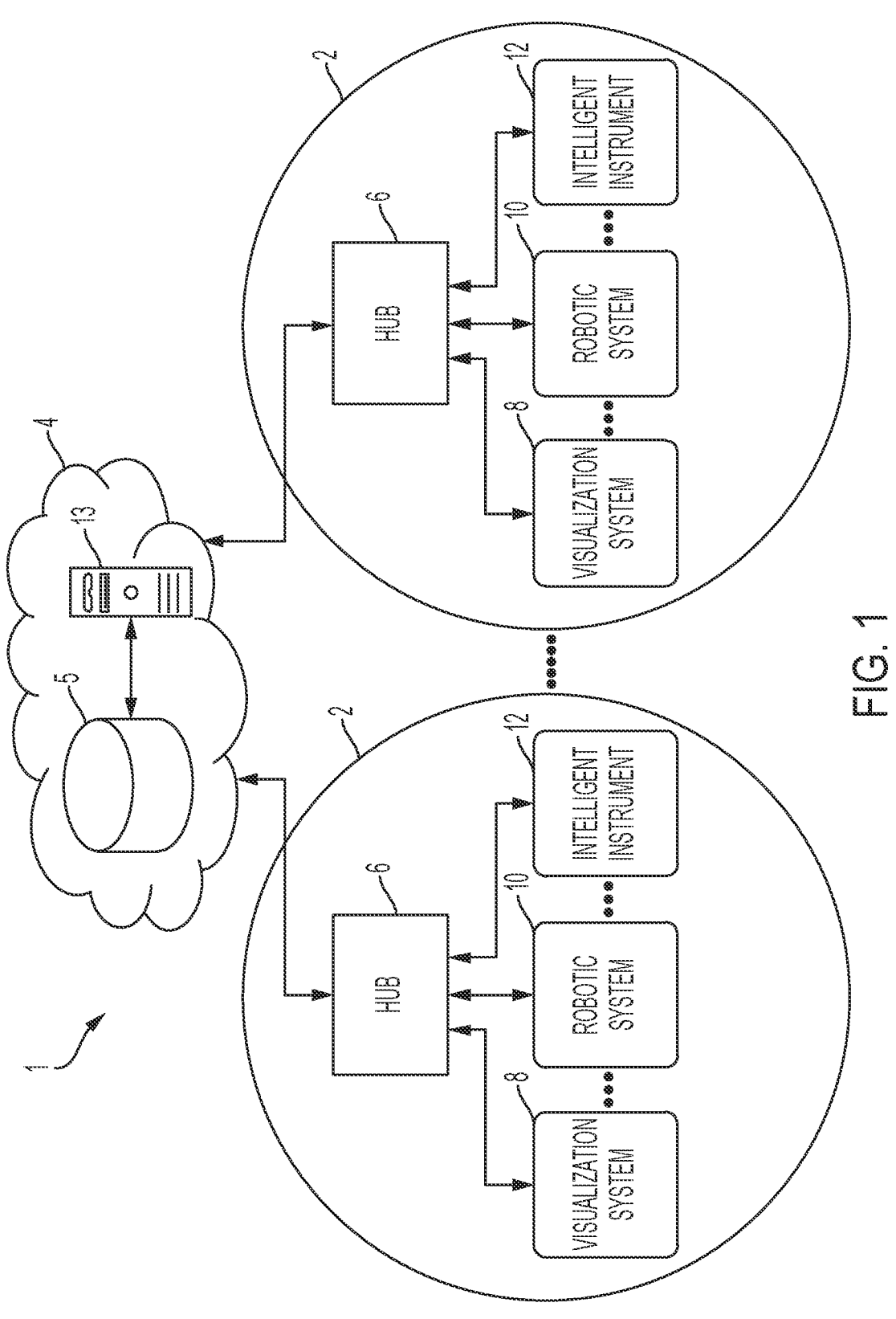
FIG. 1 is a block diagram of a computer-implemented interactive surgical system, according to one aspect of this disclosure.

Applicant of the present application owns the following U.S. patent applications filed concurrently herewith, the disclosures of each of which is herein incorporated by reference in its entirety:

U.S. patent application Ser. No. 17/688,589, titled METHOD FOR INTRAOPERATIVE DISPLAY FOR SURGICAL SYSTEMS;

U.S. patent application Ser. No. 17/688,597, titled UTILIZATION OF SURGICAL DATA VALUES AND SITUATIONAL AWARENESS TO CONTROL THE OVERLAY IN SURGICAL FIELD VIEW;

U.S. patent application Ser. No. 17/688,605, titled SELECTIVE AND ADJUSTABLE MIXED REALITY OVERLAY IN SURGICAL FIELD VIEW;

U.S. patent application Ser. No. 17/688,615, titled RISK BASED PRIORITIZATION OF DISPLAY ASPECTS IN SURGICAL FIELD VIEW;

U.S. patent application Ser. No. 17/688,626, titled SYSTEMS AND METHODS FOR CONTROLLING SURGICAL DATA OVERLAY;

U.S. patent application Ser. No. 17/688,638, titled CUSTOMIZATION OF OVERLAID DATA AND CONFIGURATION;

U.S. patent application Ser. No. 17,688,641, titled INDICATION OF THE COUPLE PAIR OF REMOTE CONTROLS WITH REMOTE DEVICES FUNCTIONS;

U.S. patent application Ser. No. 17,688,646, titled COOPERATIVE OVERLAYS OF INTERACTING INSTRUMENTS WHICH RESULT IN BOTH OVERLAYS BEING EFFECTED;

U.S. patent application Ser. No. 17/688,651, titled ANTICIPATION OF INTERACTIVE UTILIZATION OF COMMON DATA OVERLAYS BY DIFFERENT USERS;

U.S. patent application Ser. No. 17/688,653, titled MIXING DIRECTLY VISUALIZED WITH RENDERED ELEMENTS TO DISPLAY BLENDED ELEMENTS AND ACTIONS HAPPENING ON-SCREEN AND OFF-SCREEN;

U.S. patent application Ser. No. 17/688,655, titled SYSTEM AND METHOD FOR TRACKING A PORTION OF THE USER AS A PROXY FOR NON-MONITORED INSTRUMENT;

U.S. patent application Ser. No. 17/688,656, titled UTILIZING CONTEXTUAL PARAMETERS OF ONE OR MORE SURGICAL DEVICES TO PREDICT A FREQUENCY INTERVAL FOR DISPLAYING SURGICAL INFORMATION;

U.S. patent application Ser. No. 17/688,660, titled COOPERATION AMONG MULTIPLE DISPLAY SYSTEMS TO PROVIDE A HEALTHCARE USER CUSTOMIZED INFORMATION;

U.S. patent application Ser. No. 17/688,663, titled INTRAOPERATIVE DISPLAY FOR SURGICAL SYSTEMS;

U.S. patent application Ser. No. 17,688,667, titled ADAPTATION AND ADJUSTABILITY OR OVERLAID INSTRUMENT INFORMATION FOR SURGICAL SYSTEMS; and U.S. patent application No. 17/688,671, titled MIXED REALITY FEEDBACK SYSTEMS THAT COOPERATE TO INCREASE EFFICIENT PERCEPTION OF COMPLEX DATA FEEDS;

Applicant of this application owns the following U.S. patent applications, the disclosure of each of which is herein incorporated by reference in its entirety:

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Publication No. US-2019-0200981-A1;

U.S. patent application Ser. No. 16/209,453, titled METHOD FOR CONTROLLING SMART ENERGY DEVICES, now U.S. Patent Publication No. US-2019-0201046-A1.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to onscreen displays for surgical systems for a variety of energy and surgical stapler based medical devices. Energy based medical devices include, without limitation, radio-frequency (RF) based monopolar and bipolar electrosurgical instruments, ultrasonic surgical instruments, combination RF electrosurgical and ultrasonic instruments, combination RF electrosurgical and mechanical staplers, among others. Surgical stapler devices include and combined surgical staplers with electrosurgical and/or ultrasonic devices. Aspects of the ultrasonic surgical devices can be configured for transecting and/or coagulating tissue during surgical procedures, for example. Aspects of the electrosurgical devices can be configured for transecting, coagulating, sealing, welding and/or desiccating tissue during surgical procedures, for example. Aspects of the surgical stapler devices can be configured for transecting and stapling tissue during surgical procedures and in some aspects, the surgical stapler devices may be configured to delivery RF energy to the tissue during surgical procedures. Electrosurgical devices are configured to deliver therapeutic and/or nontherapeutic RF energy to the tissue. Elements of surgical staplers, electrosurgical, and ultrasonic devices may be used in combination in a single surgical instrument.

In various aspects, the present disclosure provides onscreen displays of real time information to the OR team during a surgical procedure. In accordance with various aspects of the present disclosure, many new and unique onscreen displays are provided to display onscreen a variety of visual information feedback to the OR team. According to the present disclosure, visual information may comprise one or more than one of various visual media with or without sound. Generally, visual information comprises still photography, motion picture photography, video or audio recording, graphic arts, visual aids, models, display, visual presentation services, and the support processes. The visual information can be communicated on any number of display options such as the primary OR screen, the energy or surgical stapler device itself, a tablet, augmented reality glasses, among others, for example.

In various aspects, the present disclosure provides a large list of potential options to communicate visual information in real time to the OR team, without overwhelming the OR team with too much visual information. For example, in various aspects, the present disclosure provides onscreen displays of visual information to enable the surgeon, or other members of the OR team, to selectively activate onscreen displays such as icons surrounding the screen option to manage a wealth of visual information. One or a combination of factors can be used to determine the active display, these may include energy based (e.g., electrosurgical, ultrasonic) or mechanical based (e.g., staplers) surgical devices in use, the estimated risk associated with a given display, the experience level of the surgeon and the surgeons' choice among other things. In other aspect, the visual information may comprises rich data overlaid or superimposed into the surgical field of view to manage the visual information. In various aspects described hereinbelow, comprise superimposed imagery that requires video analysis and tracking to properly overlay the data. Visual information data communicated in this manner, as opposed to static icons, may provide additional useful visual information in a more concise and easy to understand way to the OR team.

In various aspects, the present disclosure provides techniques for selectively activating onscreen displays such as icons surrounding the screen to manage visual information during a surgical procedure. In other aspects, the present disclosure provides techniques for determining the active display using one or a combination of factors. In various aspects, the techniques according to the resent disclosure may comprise selecting the energy based or mechanical based surgical device in use as the active display, estimating risk associated with a given display, utilizing the experience level of the surgeon or OR team making the selection, among other things.

In other aspects, the techniques according to the present disclosure may comprise overlaying or superimposing rich data onto the surgical field of view to manage the visual information. A number of the display arrangements described by the present disclosure involve overlaying various visual representations of surgical data onto a livestream of a surgical field. As used herein the term overlay comprises a translucent overlay, a partial overlay, and/or a moving overlay. Graphical overlays may be in the form of a transparent graphic, semitransparent graphic, or opaque graphic, or a combination of transparent, semitransparent, and opaque elements or effects. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values. The graphical overlays are rendered on top of the active display monitor to convey important information quickly and efficiently to the OR team.

In other aspects, the techniques according to the present disclosure may comprise superimposing imagery that requires analyzing video and tracking for properly overlaying the visual information data. In other aspects, the techniques according to the present disclosure may comprise communicating rich visual information, as opposed to simple static icons, to provide additional visual information to the OR team in a more concise and easy to understand manner. In other aspects, the visual overlays may be used in combination with audible and/or somatosensory overlays such as thermal, chemical, and mechanical devices, and combinations thereof.

The following description is directed generally to apparatuses, systems, and methods that provide an augmented reality (AR) interactive experience during a surgical procedure. In this context, images of a surgical field and surgical instruments and other objects appearing in the surgical field are enhanced by overlaying computer-generated visual, auditory, haptic, somatosensory, olfactory, or other sensory information onto the real world images of the surgical field, instruments, and/or other objects appearing in the surgical field. The images may be streamed in real time or may be still images. Augmented reality is a technology for rendering and displaying virtual or "augmented" virtual objects, data, or visual effects overlaid on a real environment. The real environment may include a surgical field. The virtual objects overlaid on the real environment may be represented as anchored or in a set position relative to one or more aspects of the real environment. In a non-limiting example, if a real world object exits the real environment field of view, a virtual object anchored to the real world object would also exit the augmented reality field of view.

A number of the display arrangements described by the present disclosure involve overlaying various visual representations of surgical data onto a livestream of a surgical field. As used herein the term overlaying comprises a translucent overlay, a partial overlay, and/or a moving overlay. Moreover, the overlay can be positioned on, or at least partially on, or near an object in the surgical field such as, for example, an end effector and/or a critical surgical structure. Certain display arrangements may comprise a change in one or more display elements of an overlay including a change in color, size, shape, display time, display location, display frequency, highlighting, or a combination thereof, based on changes in display priority values.

As described herein AR is an enhanced version of the real physical world that is achieved through the use of digital visual elements, sound, or other sensory stimuli delivered via technology. Virtual Reality (VR) is a computer-generated environment with scenes and objects that appear to be real, making the user feel they are immersed in their surroundings. This environment is perceived through a device known as a Virtual Reality headset or helmet. Mixed reality (MR) and AR are both considered immersive technologies, but they aren't the same. MR is an extension of Mixed reality that allows real and virtual elements to interact in an environment. While AR adds digital elements to a live view often by using a camera, an MR experience combines elements of both AR and VR, where real-world and digital objects interact.

In an AR environment, one or more computer-generated virtual objects may be displayed along with one or more real (i.e., so-called "real world") elements. For example, a real-time image or video of a surrounding environment may be shown on a computer screen display with one or more overlaying virtual objects. Such virtual objects may provide complementary information relating to the environment or generally enhance a user's perception and engagement with the environment. Conversely, the real-time image or video of the surrounding environment may additionally or alternatively enhance a user's engagement with the virtual objects shown on the display.

The apparatuses, systems, and methods in the context of this disclosure enhance images received from one or more imaging devices during a surgical procedure. The imaging devices may include a variety of scopes used during non-invasive and minimally invasive surgical procedures, an AR device, and/or a camera to provide images during open surgical procedures. The images may be streamed in real time or may be still images. The apparatuses, systems, and methods provide an augmented reality interactive experience by enhancing images of the real world surgical environment by overlaying virtual objects or representations of data and/or real objects onto the real surgical environment. The augmented reality experience may be viewed on a display and/or an AR device that allows a user to view the overlaid virtual objects onto the real world surgical environment. The display may be located in the operating room or remote from the operating room. AR devices are worn on the head of the surgeon or other operating room personnel and typically include two stereo-display lenses or screens, including one for each eye of the user. Natural light is permitted to pass through the two transparent or semi-transparent display lenses such that aspects of the real environment are visible while also projecting light to make virtual objects visible to the user of the AR device.

Two or more displays and AR devices may be used in a coordinated manner, for example with a first display or AR device controlling one or more additional displays or AR devices in a system with defined roles. For example, when activating display or an AR device, a user may select a role (e.g., surgeon, surgical assistant, nurse, etc., during a surgical procedure) and the display or AR device may display information relevant to that role. For example, a surgical assistant may have a virtual representation of an instrument displayed that the surgeon needs to perform for a next step of a surgical procedure. A surgeon's focus on the current step may see different information displayed than the surgical assistant.

Although there are many known onscreen displays and alerts, this disclosure provides many new and unique augmented reality interactive experiences during a surgical procedure. Such augmented reality interactive experiences include visual, auditory, haptic, somatosensory, olfactory, or other sensory feedback information to the surgical team inside or outside the operating room. The virtual feedback information overlaid onto the real world surgical environment may be provided to an operating room (OR) team, including personnel inside the OR including, without limitation, the operating surgeon, assistants to the surgeon, a scrub person, an anesthesiologist and a circulating nurse, among others, for example. The virtual feedback information can be communicated on any number of display options such as a primary OR screen display, an AR device, the energy or surgical stapler instrument, a tablet, augmented reality glasses, device etc.

FIG. 1 depicts a computer-implemented interactive surgical system 1 that includes one or more surgical systems 2 and a cloud-based system 4. The cloud-based system 4 may include a remote server 13 coupled to a storage device 5. Each surgical system 2 includes at least one surgical hub 6 in communication with the cloud 4. For example, the surgical system 2 may include a visualization system 8, a robotic system 10, and handheld intelligent surgical instruments 12, each configured to communicate with one another and/or the hub 6. In some aspects, a surgical system 2 may include an M number of hubs 6, an N number of visualization systems 8, an O number of robotic systems 10, and a P number of handheld intelligent surgical instruments 12, where M, N, O, and P are integers greater than or equal to one. The computer-implemented interactive surgical system 1 may be configured to provide an augmented reality interactive experience during a surgical procedure as described herein.

Figure 2:
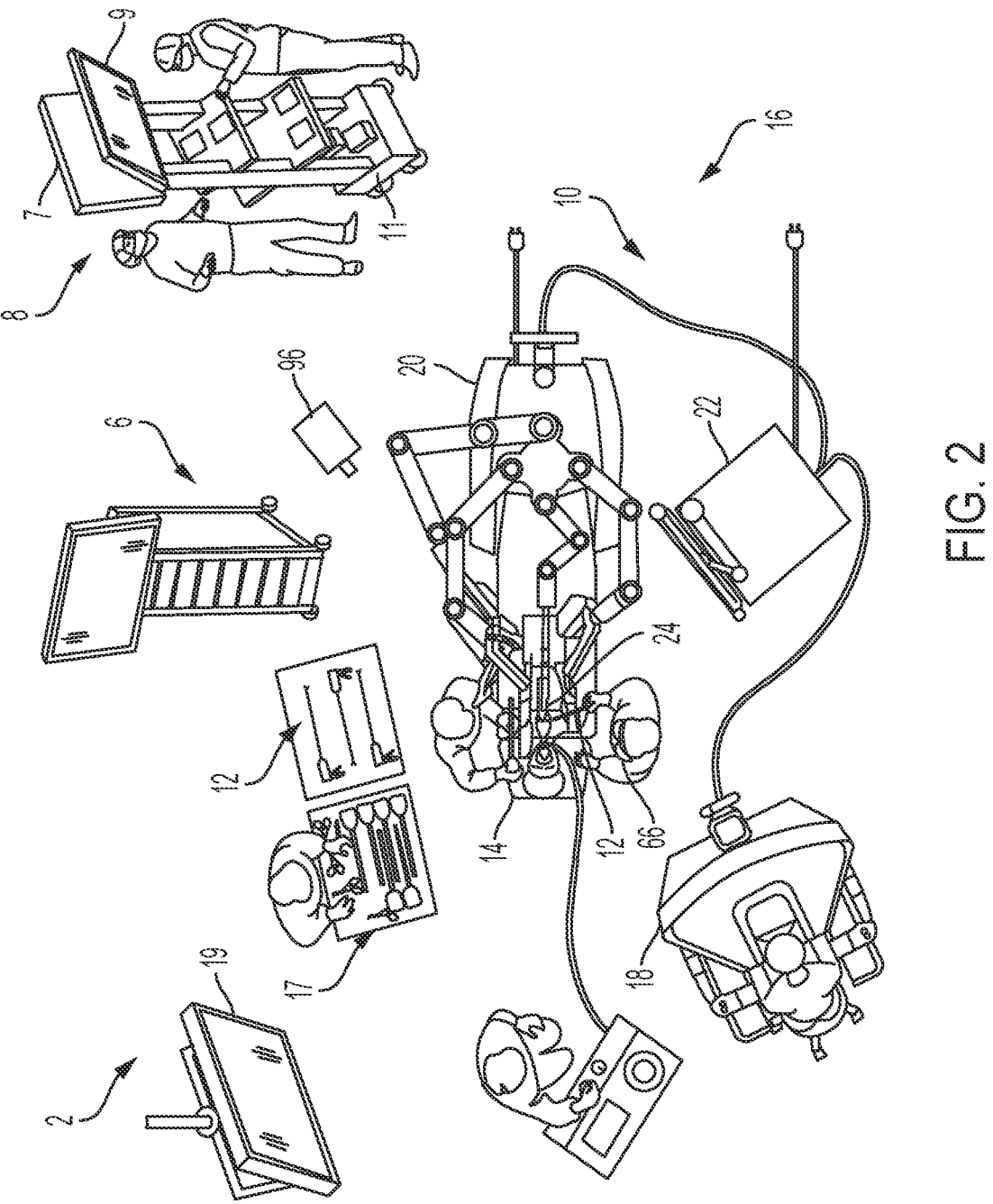
FIG. 2 is a surgical system being used to perform a surgical procedure in an operating room, according to one aspect of this disclosure.

FIG. 2 depicts an example of a surgical system 2 to perform a surgical procedure on a patient lying down on an operating table 14 in a surgical operating room 16. A robotic system 10 is used in the surgical procedure as a part of the surgical system 2. The robotic system 10 includes a surgeon's console 18, a patient side cart 20 (surgical robot), and a surgical robotic hub 22. The patient side cart 20 can manipulate at least one removably coupled surgical tool 17 through a minimally invasive incision in the body of the patient while the surgeon views the surgical site through the surgeon's console 18 or an augmented reality (AR) device 66 worn by the surgeon. An image (e.g., still or live streamed in real time) of the surgical site during a minimally invasive procedure can be obtained by a medical imaging device 24. The patient side cart 20 can manipulate the imaging device 24 to orient the imaging device 24. An image of an open surgical procedure can be obtained by a medical imaging device 96. The robotic hub 22 processes the images of the surgical site for subsequent display on the surgeon's console 18 or the AR device 66 worn by the surgeon, or other person in the surgical operating room 16.

The optical components of the imaging device 24, 96 or AR device 66 may include one or more illumination sources and/or one or more lenses. The one or more illumination sources may be directed to illuminate portions of the surgical field. One or more image sensors may receive light reflected or refracted from tissue and instruments in the surgical field.

In various aspects, the imaging device 24 is configured for use in a minimally invasive surgical procedure. Examples of imaging devices suitable for use with this disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope. In various aspects, the imaging device 96 is configured for use in an open (invasive) surgical procedure.

In various aspects, the visualization system 8 includes one or more imaging sensors, one or more image-processing units, one or more storage arrays, and one or more displays that are strategically arranged with respect to the sterile field. In one aspect, the visualization system 8 includes an interface for HL7, PACS, and EMR. In one aspect, the imaging device 24 may employ multi-spectrum monitoring to discriminate topography and underlying structures. A multi-spectral image captures image data within specific wavelength ranges in the electromagnetic spectrum. Wavelengths are separated by filters or instruments sensitive to particular wavelengths, including light from frequencies beyond the visible light range, e.g., IR and ultraviolet. Spectral imaging can extract information not visible to the human eye. Multi-spectrum monitoring can relocate a surgical field after a surgical task is completed to perform tests on the treated tissue.

FIG. 2 depicts a primary display 19 positioned in the sterile field to be visible to an operator at the operating table 14. A visualization tower 11 is positioned outside the sterile field and includes a first non-sterile display 7 and a second non-sterile display 9, which face away from each other. The visualization system 8, guided by the hub 6, is configured to utilize the displays 7, 9, 19 to coordinate information flow to operators inside and outside the sterile field. For example, the hub 6 may cause the visualization system 8 to display AR images of the surgical site, as recorded by an imaging device 24, 96 on a non-sterile display 7, 9, or through the AR device 66, while maintaining a live feed of the surgical site on the primary display 19 or the AR device 66. The non-sterile display 7, 9 can permit a non-sterile operator to perform a diagnostic step relevant to the surgical procedure, for example.

Figure 3:
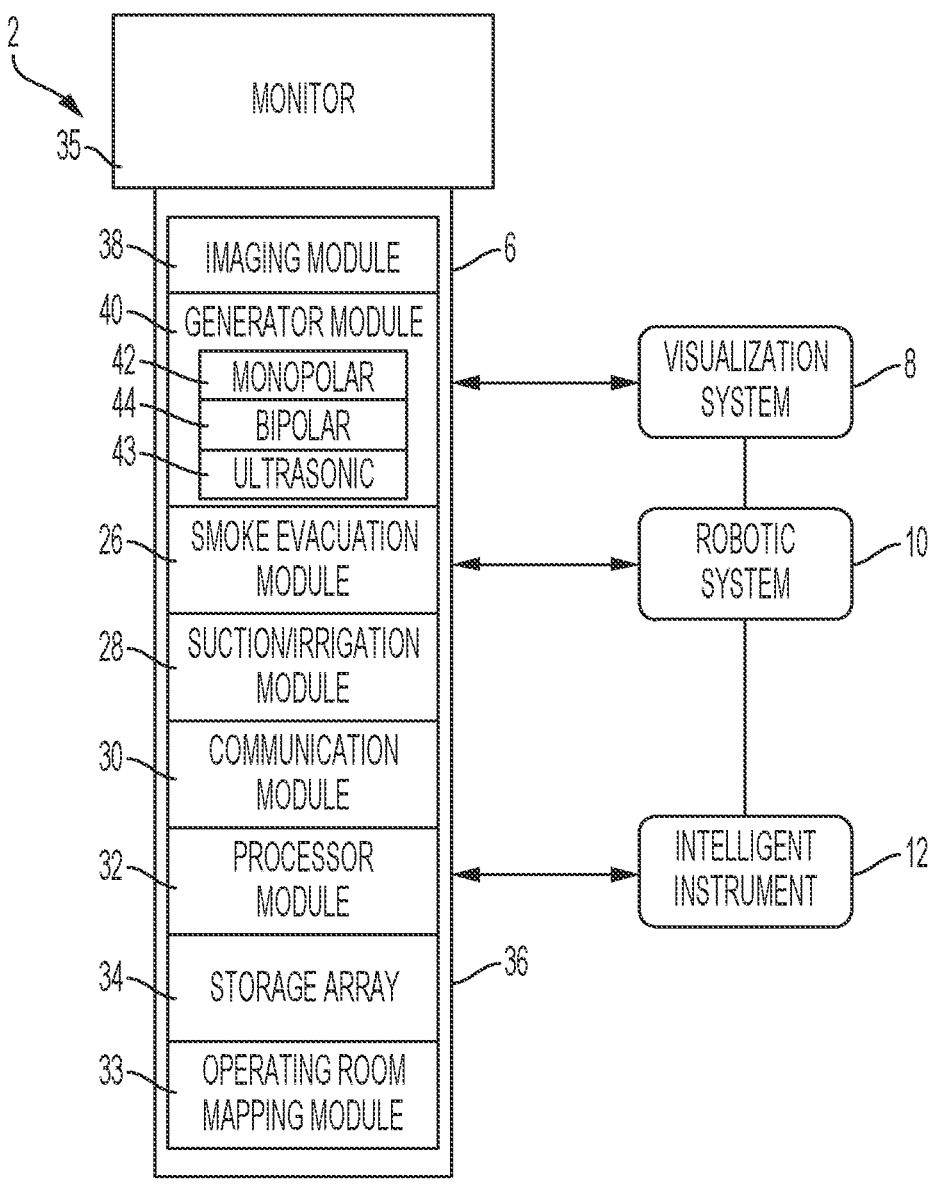
FIG. 3 is a surgical hub paired with a visualization system, a robotic system, and an intelligent instrument, according to one aspect of this disclosure.
Figure 10:
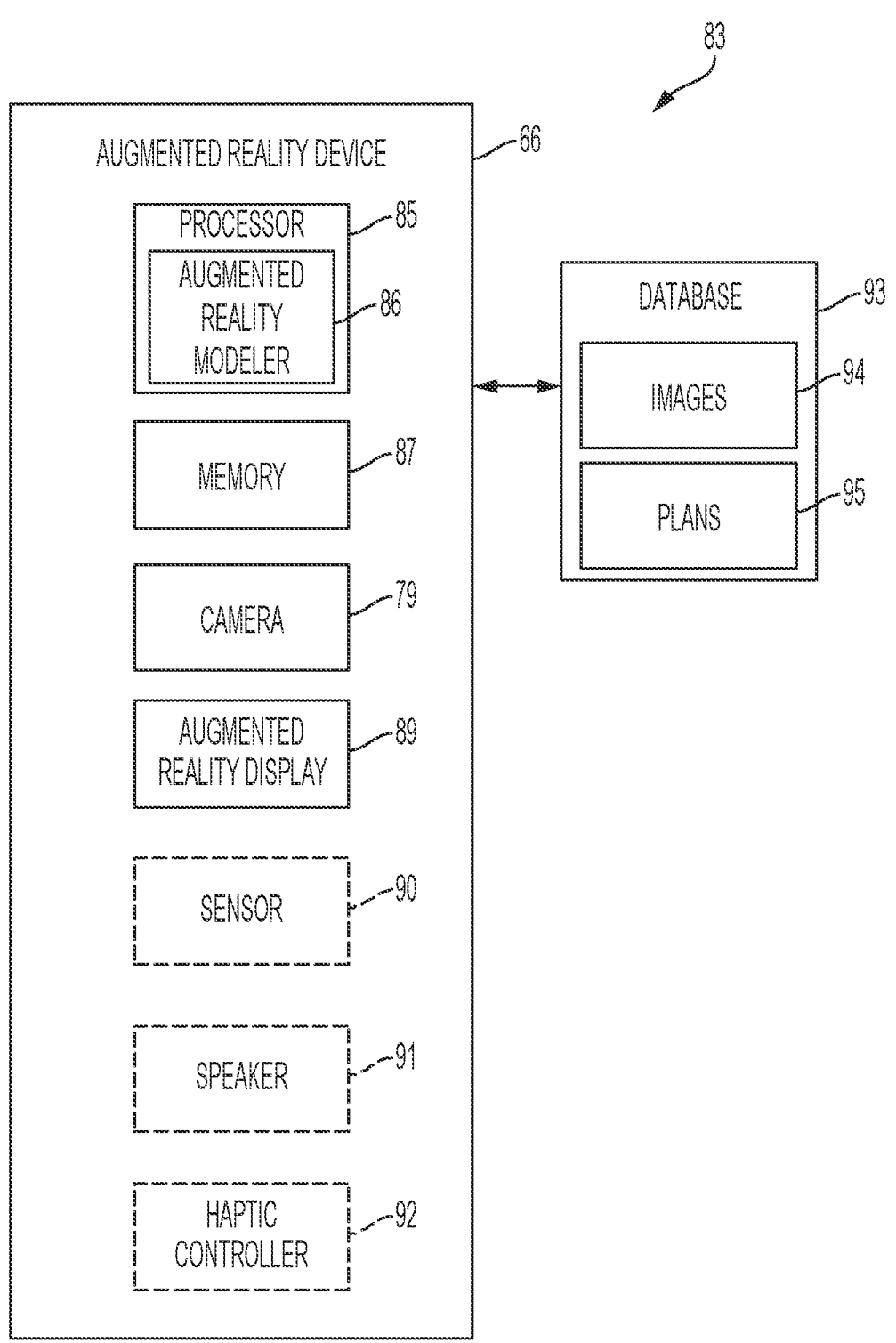
FIG. 10 illustrates a system for augmenting surgical instrument information using an augmented reality display, according to one aspect of this disclosure.

FIG. 3 depicts a hub 6 in communication with a visualization system 8, a robotic system 10, and a handheld intelligent surgical instrument 12. The hub 6 includes a hub display 35, an imaging module 38, a generator module 40, a communication module 30, a processor module 32, a storage array 34, and an operating room mapping module 33. The hub 6 further includes a smoke evacuation module 26 and/or a suction/irrigation module 28. In various aspects, the imaging module 38 comprises an AR device 66 and the processor module 32 comprises an integrated video processor and an augmented reality modeler (e.g., as shown in FIG. 10). A modular light source may be adapted for use with various imaging devices. In various examples, multiple imaging devices may be placed at different positions in the surgical field to provide multiple views (e.g., non-invasive, minimally invasive, invasive or open surgical procedures). The imaging module 38 can be configured to switch between the imaging devices to provide an optimal view. In various aspects, the imaging module 38 can be configured to integrate the images from the different imaging devices and provide an augmented reality interactive experience during a surgical procedure as described herein.

Figure 4:
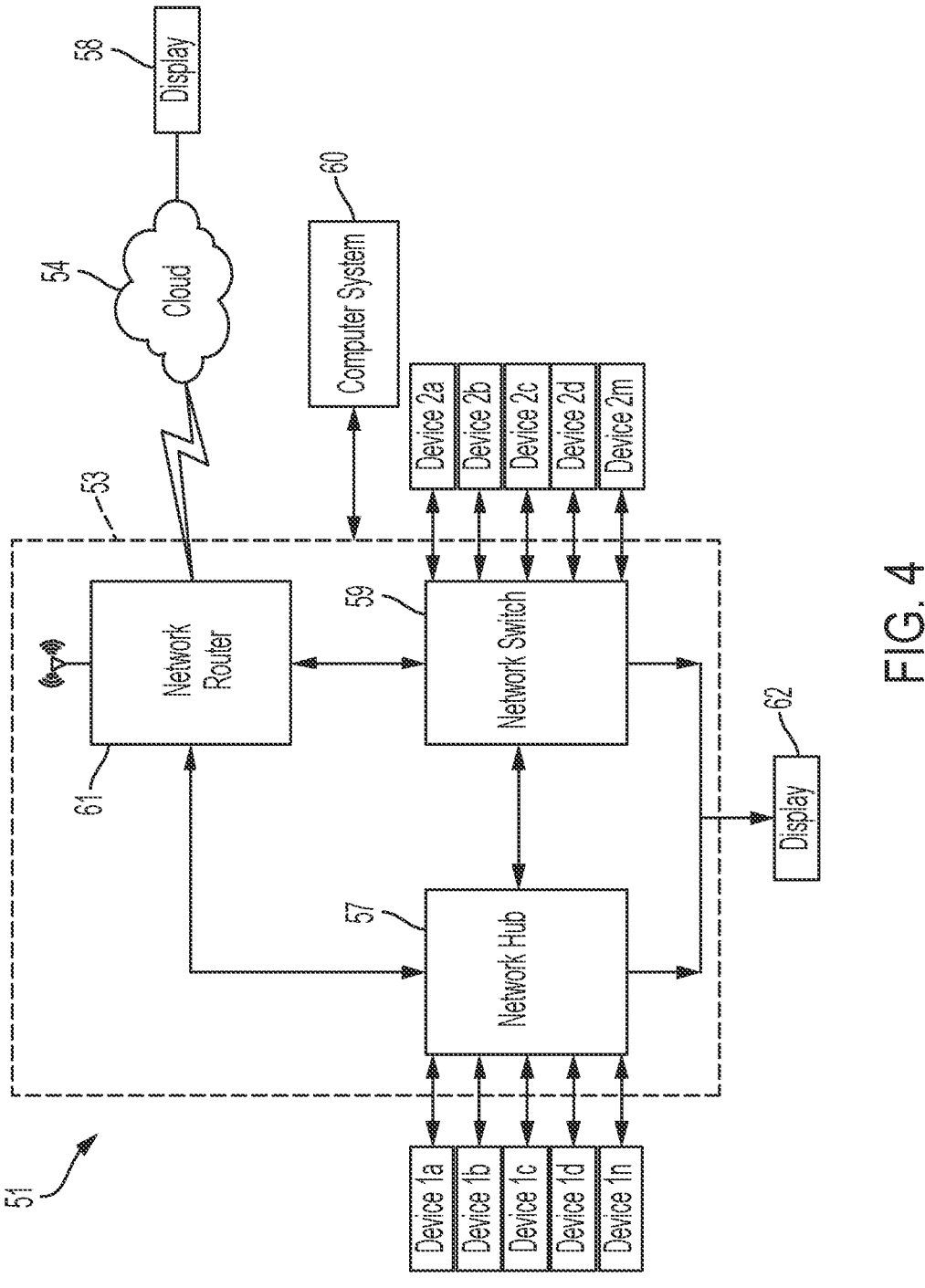
FIG. 4 illustrates a surgical data network comprising a modular communication hub configured to connect modular devices located in one or more operating theaters of a healthcare facility, or any room in a healthcare facility specially equipped for surgical operations, to the cloud, according to one aspect of this disclosure.

FIG. 4 shows a surgical data network 51 comprising a modular communication hub 53 configured to connect modular devices located in one or more operating theaters/rooms of a healthcare facility to a cloud-based system. The cloud 54 may include a remote server 63 (FIG. 5) coupled to a storage device 55. The modular communication hub 53 comprises a network hub 57 and/or a network switch 59 in communication with a network router 61. The modular communication hub 53 is coupled to a local computer system 60 to process data. Modular devices 1a-1n in the operating theater may be coupled to the modular communication hub 53. The network hub 57 and/or the network switch 59 may be coupled to a network router 61 to connect the devices 1a-1n to the cloud 54 or the local computer system 60. Data associated with the devices 1a-1n may be transferred to cloud-based computers via the router for remote data processing and manipulation. The operating theater devices 1a-1n may be connected to the modular communication hub 53 over a wired channel or a wireless channel. The surgical data network 51 environment may be employed to provide an augmented reality interactive experience during a surgical procedure as described herein and in particular providing augmented images if the surgical field to one or more than one remote display 58.

Figure 5:
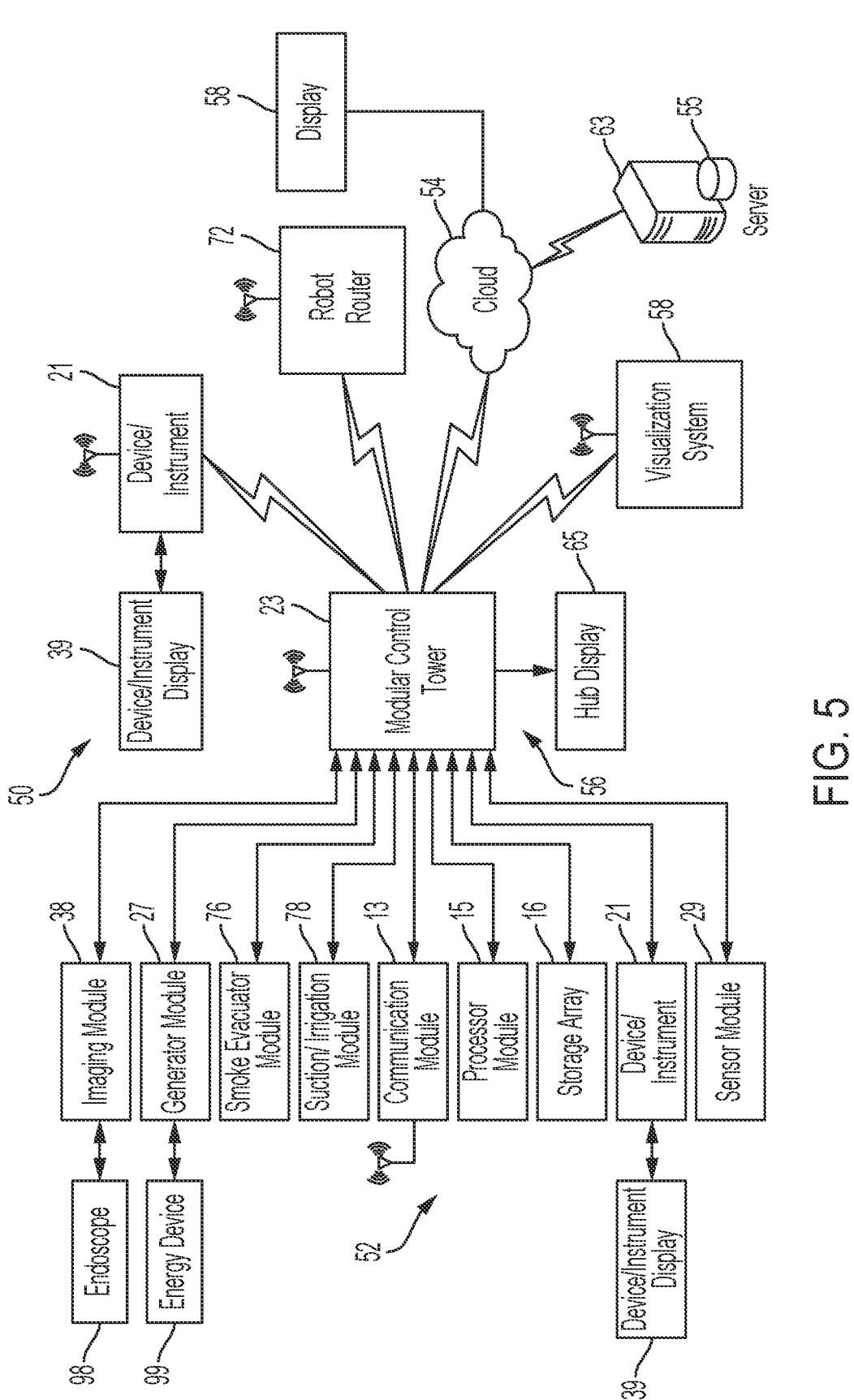
FIG. 5 illustrates a computer-implemented interactive surgical system, according to one aspect of this disclosure.
Figure 6:
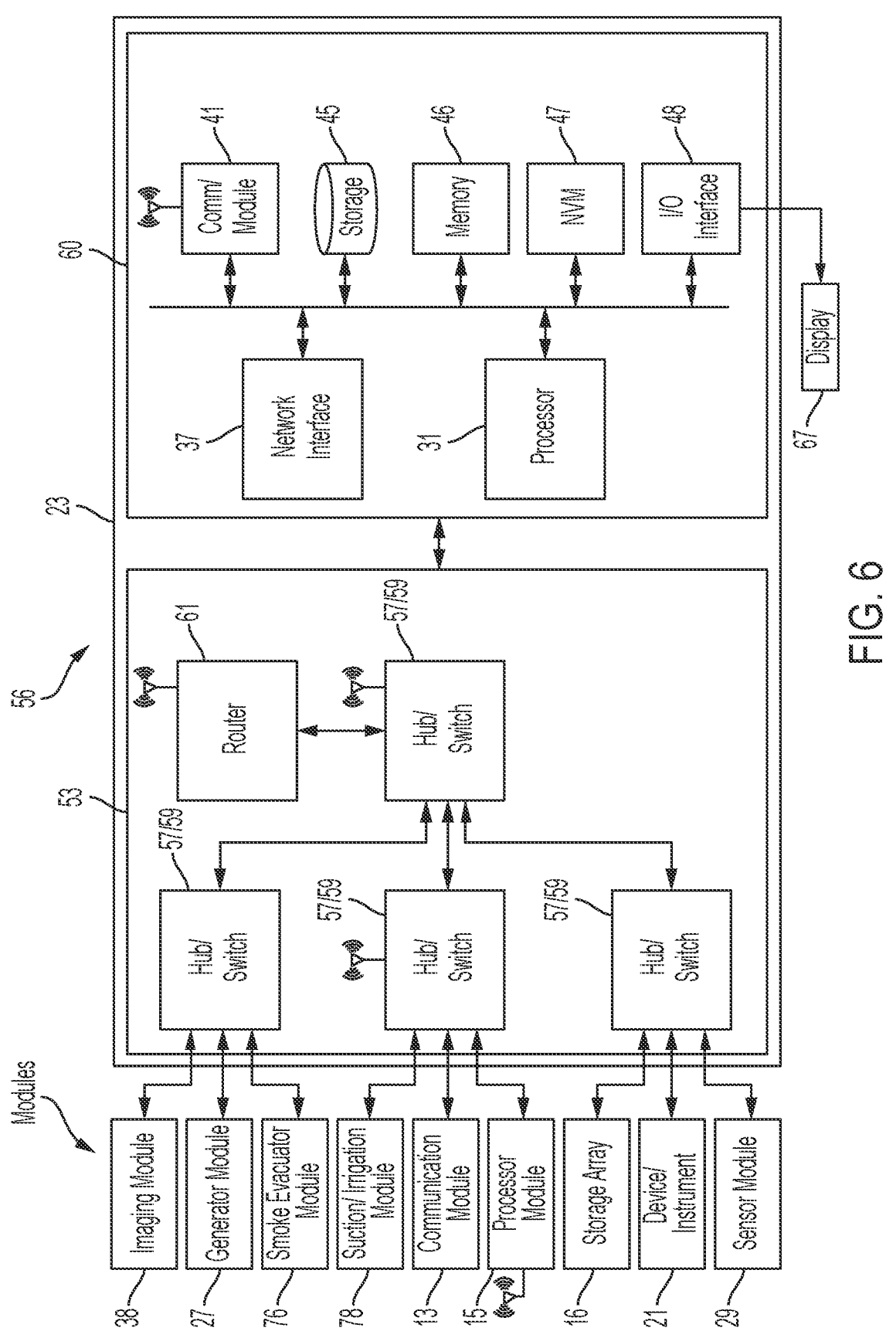
FIG. 6 illustrates a surgical hub comprising a plurality of modules coupled to the modular control tower, according to one aspect of this disclosure.

FIG. 5 illustrates a computer-implemented interactive surgical system 50. The computer-implemented interactive surgical system 50 is similar in many respects to the computer-implemented interactive surgical system 1. The computer-implemented interactive surgical system 50 includes one or more surgical systems 52, which are similar in many respects to the surgical systems 2. Each surgical system 52 includes at least one surgical hub 56 in communication with a cloud 54 that may include a remote server 63. In one aspect, the computer-implemented interactive surgical system 50 comprises a modular control tower 23 connected to multiple operating theater devices such as, for example, intelligent surgical instruments, robots, and other computerized devices located in the operating theater. As shown in FIG. 6, the modular control tower 23 comprises a modular communication hub 53 coupled to a computer system 60.

Back to FIG. 5, the modular control tower 23 is coupled to an imaging module 38 that is coupled to an endoscope 98, a generator module 27 that is coupled to an energy device 99, a smoke evacuator module 76, a suction/irrigation module 78, a communication module 13, a processor module 15, a storage array 16, a smart device/instrument 21 optionally coupled to a display 39, and a sensor module 29. The operating theater devices are coupled to cloud computing resources such as server 63, data storage 55, and displays 58 via the modular control tower 23. A robot hub 72 also may be connected to the modular control tower 23 and to the servers 63, data storage 55, and displays 58. The devices/instruments 21, visualization systems 58, among others, may be coupled to the modular control tower 23 via wired or wireless communication standards or protocols, as described herein. The modular control tower 23 may be coupled to a hub display 65 (e.g., monitor, screen) to display augmented images received comprising overlaid virtual objects on the real surgical field received from the imaging module 38, device/instrument display 39, and/or other visualization systems 58. The hub display 65 also may display data received from devices connected to the modular control tower 23 in conjunction with images and overlaid images.

FIG. 6 illustrates a surgical hub 56 comprising a plurality of modules coupled to the modular control tower 23. The modular control tower 23 comprises a modular communication hub 53, e.g., a network connectivity device, and a computer system 60 to provide local processing, visualization, and imaging of augmented surgical information, for example. The modular communication hub 53 may be connected in a tiered configuration to expand the number of modules (e.g., devices) that may be connected to the modular communication hub 53 and transfer data associated with the modules to the computer system 60, cloud computing resources, or both. Each of the network hubs/switches 57, 59 in the modular communication hub 53 may include three downstream ports and one upstream port. The upstream network hub/switch 57, 59 is connected to a processor 31 to provide a communication connection to the cloud computing resources and a local display 67. Communication to the cloud 54 may be made either through a wired or a wireless communication channel.

The computer system 60 comprises a processor 31 and a network interface 37. The processor 31 is coupled to a communication module 41, storage 45, memory 46, non-volatile memory 47, and input/output interface 48 via a system bus. The system bus can be any of several types of bus structure(s) including the memory bus or memory controller, a peripheral bus or external bus, and/or a local bus using any variety of available bus architectures.

The processor 31 comprises an augmented reality modeler (e.g., as shown in FIG. 10) and may be implemented as a single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital convert-ers (ADCs) with 12 analog input channels, details of which are available for the product datasheet.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes ran-dom-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SL-DRAM), and direct Rambus RAM (DRRAM).

The computer system 60 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

In various aspects, the computer system 60 of FIG. 6, the imaging module 38 and/or visualization system 58, and/or the processor module 15 of FIGS. 4-6, may comprise an image processor, image-processing engine, graphics pro-cessing unit (GPU), media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor archi-tecture.

Figure 7:
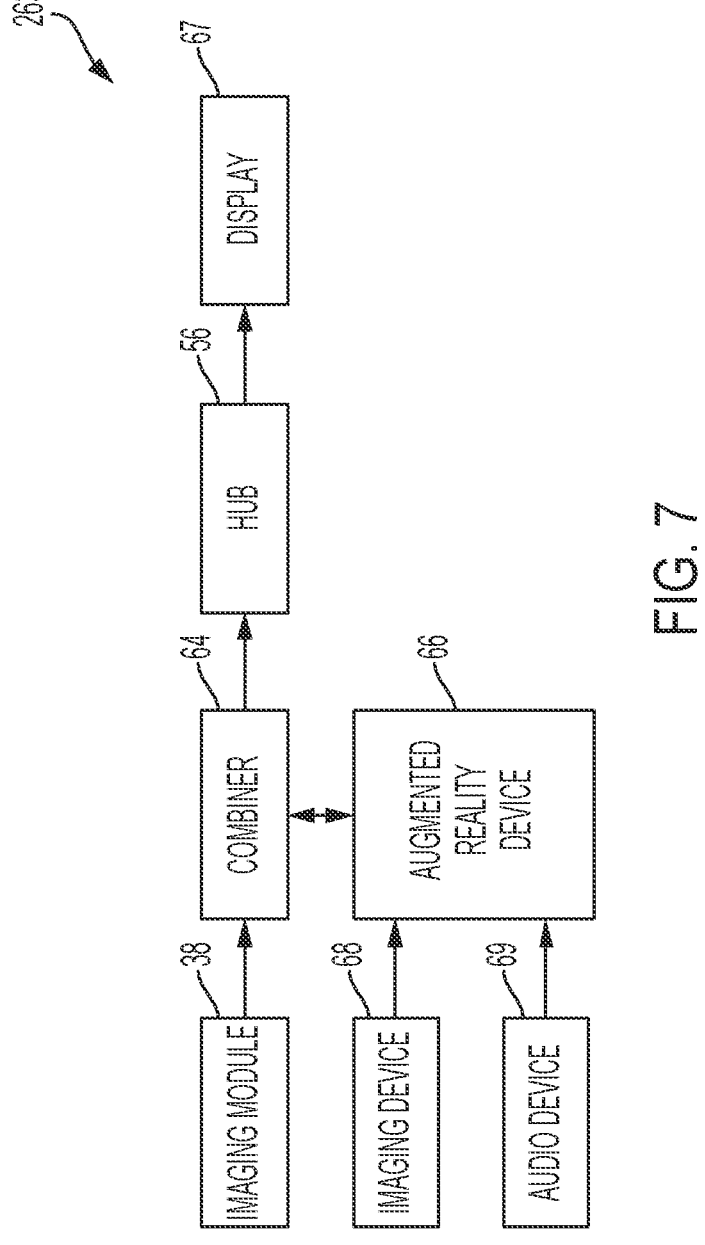
FIG. 7 illustrates an augmented reality (AR) system comprising an intermediate signal combiner positioned in the communication path between an imaging module and a surgical hub display, according to one aspect of this disclosure.

FIG. 7 illustrates an augmented reality system 263 com-prising an intermediate signal combiner 64 positioned in the communication path between an imaging module 38 and a surgical hub display 67. The signal combiner 64 combines audio and/or image data received from an imaging module 38 and/or an AR device 66. The surgical hub 56 receives the combined data from the combiner 64 and overlays the data provided to the display 67, where the overlaid data is displayed. The imaging device 68 may be a digital video camera and the audio device 69 may be a microphone. The signal combiner 64 may comprise a wireless heads-up display adapter to couple to the AR device 66 placed into the communication path of the display 67 to a console allowing the surgical hub 56 to overlay data on the display 67.

Figure 8:
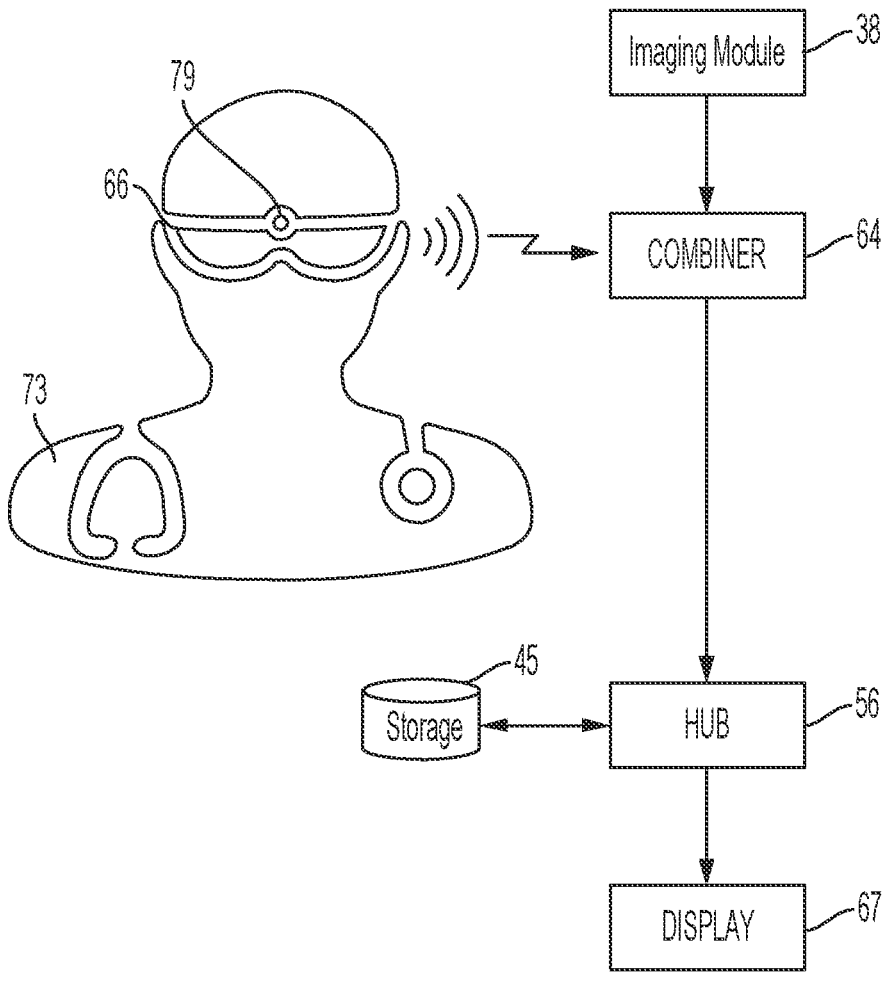
FIG. 8 illustrates an augmented reality (AR) system comprising an intermediate signal combiner positioned in the communication path between an imaging module and a surgical hub display, according to one aspect of this disclosure.

FIG. 8 illustrates an augmented reality (AR) system comprising an intermediate signal combiner positioned in the communication path between an imaging module and a surgical hub display. FIG. 8 illustrates an AR device 66 worn by a surgeon 73 to communicate data to the surgical hub 56. Peripheral information of the AR device 66 does not include active video. Rather, the peripheral information includes only device settings, or signals that do not have same demands of refresh rates. Interaction may augment the surgeon's 73 information based on linkage with preoperative computerized tomography (CT) or other data linked in the surgical hub 56. The AR device 66 can identify structure—ask whether instrument is touching a nerve, vessel, or adhesion, for example. The AR device 66 may include pre-operative scan data, an optical view, tissue interrogation properties acquired throughout procedure, and/or processing in the surgical hub 56 used to provide an answer. The surgeon 73 can dictate notes to the AR device 66 to be saved with patient data in the hub storage 45 for later use in report or in follow up.

The AR device 66 worn by the surgeon 73 links to the surgical hub 56 with audio and visual information to avoid the need for overlays, and allows customization of displayed information around periphery of view. The AR device 66 provides signals from devices (e.g., instruments), answers queries about device settings, or positional information linked with video to identify quadrant or position. The AR device 66 has audio control and audio feedback from the AR device 66. The AR device 66 is able to interact with other systems in the operating theater and have feedback and interaction available wherever the surgeon 73 is viewing. For example, the AR device 66 may receive voice or gesture initiated commands and queries from a surgeon, and the AR device 66 may provide feedback in the form of one or more modalities including audio, visual, or haptic touch.

Figure 9:
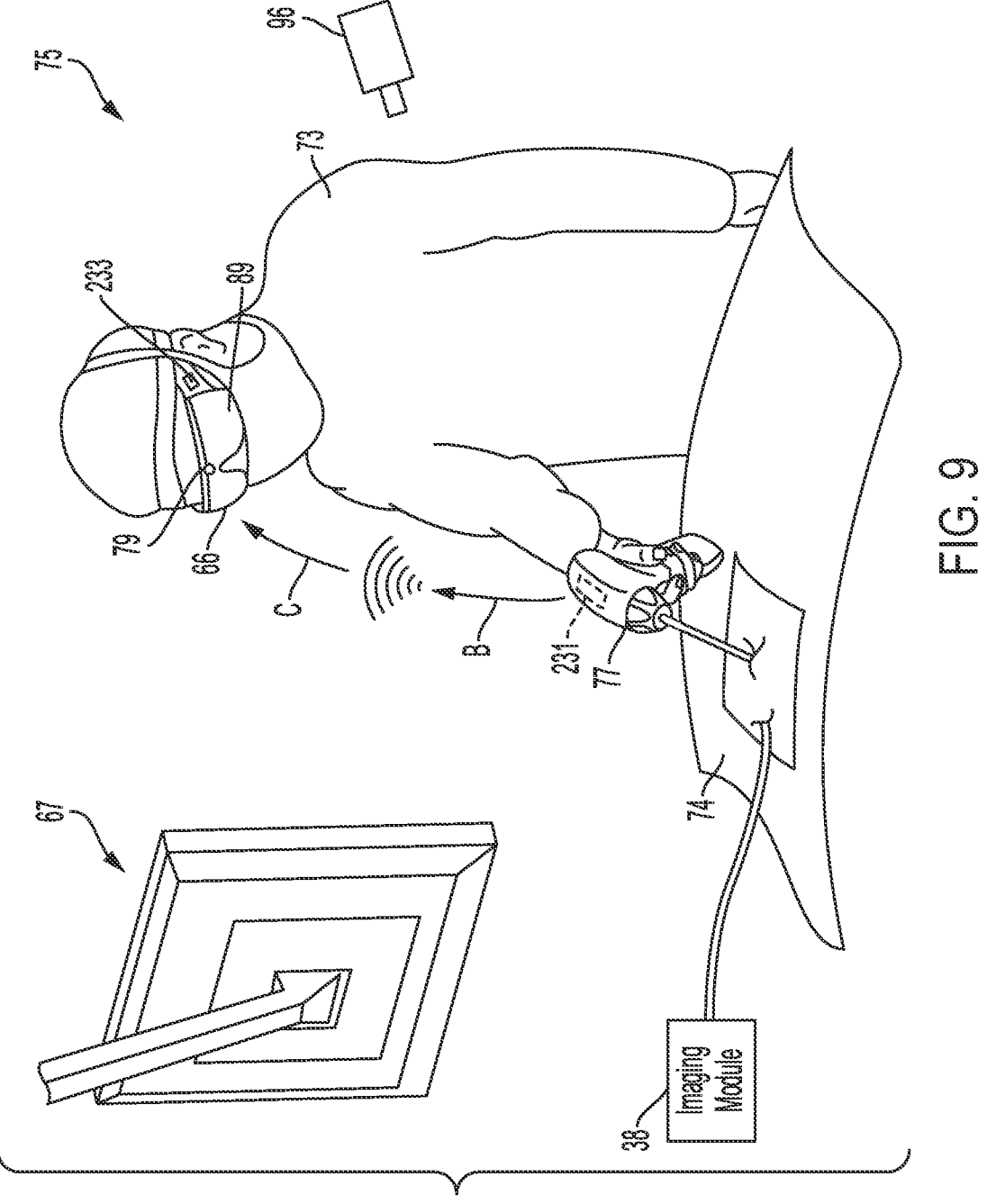
FIG. 9 illustrates an augmented reality (AR) device worn by a surgeon to communicate data to the surgical hub, according to one aspect of this disclosure.

FIG. 9 illustrates a surgeon 73 wearing an AR device 66, a patient 74, and may include a camera 96 in an operating room 75. The AR device 66 worn by the surgeon 73 may be used to present to the surgeon 73 a virtual object overlaid on a real time image of the surgical field through augmented reality display 89 or through the hub connected display 67. The real time image may include a portion of a surgical instrument 77. The virtual object may not be visible to others within the operating room 75 (e.g., surgical assistant or nurse), though they also may wear AR devices 66. Even if another person is viewing the operating room 75 with an AR device 66, the person may not be able to see the virtual object or may be able to see the virtual object in a shared augmented reality with the surgeon 73, or may be able to see a modified version of the virtual object (e.g., according to customizations unique to the surgeon 73) or may see dif-ferent virtual objects.

A virtual object and/or data may be configured to appear on a portion of a surgical instrument 77 or in a surgical field of view captured by an imaging module 38, an imaging device 68 during minimally invasive surgical procedures, and/or the camera 96 during open surgical procedures. In the illustrated example, the imaging module 38 is a laparoscopic camera that provides a live feed of a surgical area during a minimally invasive surgical procedure. An AR system may present virtual objects that are fixed to a real object without regard to a perspective of a viewer or viewers of the AR system (e.g., the surgeon 73). For example, a virtual object may be visible to a viewer of the AR system inside the operating room 75 and not visible to a viewer of the AR system outside the operating room 75. The virtual object may be displayed to the viewer outside the operating room 75 when the viewer enters the operating room 75. The augmented image may be displayed on the surgical hub display 67 or the augmented reality display 89.

The AR device 66 may include one or more screens or lens, such as a single screen or two screens (e.g., one per eye of a user). The screens may allow light to pass through the screens such that aspects of the real environment are visible while displaying the virtual object. The virtual object may be made visible to the surgeon 73 by projecting light. A virtual object may appear to have a degree of transparency or may be opaque (i.e., blocking aspects of the real environment).

An AR system may be viewable to one or more viewers, and may include differences among views available for the one or more viewers while retaining some aspects as universal among the views. For example, a heads-up display may change between two views while virtual objects and/or data may be fixed to a real object or area in both views. Aspects such as a color of an object, lighting, or other changes may be made among the views without changing a fixed position of at least one virtual object.

A user may see a virtual object and/or data presented in an AR system as opaque or as including some level of transparency. In an example, the user may interact with the virtual object, such as by moving the virtual object from a first position to a second position. For example, the user may move an object with his or her hand. This may be done in the AR system virtually by determining that the hand has moved into a position coincident or adjacent to the object (e.g., using one or more cameras, which may be mounted on the AR device 66, such as AR device camera 79 or separate 96, and which may be static or may be controlled to move), and causing the object to move in response. Virtual aspects may include virtual representations of real world objects or may include visual effects, such as lighting effects, etc. The AR system may include rules to govern the behavior of virtual objects, such as subjecting a virtual object to gravity or friction, or may include other predefined rules that defy real world physical constraints (e.g., floating objects, perpetual motion, etc.). The AR device 66 may include a camera 79 on the AR device 66 (not to be confused with the camera 96, separate from the AR device 66). The AR device camera 79 or the camera 96 may include an infrared camera, an infrared filter, a visible light filter, a plurality of cameras, a depth camera, etc. The AR device 66 may project virtual items over a representation of a real environment, which may be viewed by a user.

The AR device 66 may be used in the operating room 75 during a surgical procedure, for example performed by the surgeon 73 on the patient 74. The AR device 66 may project or display virtual objects, such as a virtual object during the surgical procedure to augment the surgeon's vision. The surgeon 73 may view a virtual object using the AR device 66, a remote controller for the AR device 66, or may interact with a virtual object, for example, using a hand to "interact" with a virtual object or a gesture recognized by the camera 79 of the AR device 66. A virtual object may augment a surgical tool such as the surgical instrument 77. For example, the virtual object may appear (to the surgeon 73 viewing the virtual object through the AR device 66) to be coupled with or remain a fixed distance from the surgical instrument 77. In another example, the virtual object may be used to guide the surgical instrument 77, and may appear to be fixed to the patient 74. In certain examples, a virtual object may react to movements of other virtual or real-world objects in the surgical field. For example, the virtual object may be altered when a surgeon is manipulating a surgical instrument in proximity to the virtual object.

The augmented reality display system imaging device 38 capture a real image of a surgical area during a surgical procedure. An augmented reality display 89, 67 presents an overlay of an operational aspect of the surgical instrument 77 onto the real image of the surgical area. The surgical instrument 77 includes communications circuitry 231 to communicate operational aspects and functional data from the surgical instrument 77 to the AR device 66 via communication communications circuitry 233 on the AR device 66. Although the surgical instrument 77 and the AR device 66 are shown in RF wireless communication between circuits 231, 233 as indicated by arrows B, C, other communication techniques may employed (e.g., wired, ultrasonic, infrared, etc.). The overlay is related to the operational aspect of the surgical instrument 77 being actively visualized. The overlay combines aspects of tissue interaction in the surgical area with functional data from the surgical instrument 77. A processor portion of the AR device 66 is configured to receive the operational aspects and functional data from the surgical instrument 77, determine the overlay related to the operation of the surgical instrument 77, and combine the aspect of the tissue in the surgical area with the functional data from the surgical instrument 77. The augmented images indicate alerts relative to device performance considerations, alerts of incompatible usage, alerts on incomplete capture. Incompatible usage includes tissue out range conditions and tissue incorrectly balanced within the jaws of the end effector. Additional augmented images provide an indication of collateral events including indication of tissue tension and indication of foreign object detection. Other augmented images indicate device status overlays and instrument indication.

FIG. 10 illustrates a system 83 for augmenting images of a surgical field with information using an AR display 89, in accordance with at least one aspect of this disclosure. The system 83 may be used to perform the techniques described hereinbelow, for example, by using the processor 85. The system 83 includes one aspect of an AR device 66 that may be in communication with a database 93. The AR device 66 includes a processor 85, memory 87, an AR display 89, and a camera 79. The AR device 66 may include a sensor 90, a speaker 91, and/or a haptic controller 92. The database 93 may include image storage 94 or preoperative plan storage 95.

The processor 85 of the AR device 66 includes an augmented reality modeler 86. The augmented reality modeler 86 may be used by the processor 85 to create the augmented reality environment. For example, the augmented reality modeler 86 may receive images of the instrument in a surgical field, such as from the camera 79 or sensor 90, and create the augmented reality environment to fit within a display image of the surgical field of view. In another example, physical objects and/or date may be overlaid on the surgical field of view and/or the surgical instruments images and the augmented reality modeler 86 may use physical objects and data to present the augmented reality display of virtual object s and/or data in the augmented reality environment. For example, the augmented reality modeler 86 may use or detect an instrument at a surgical site of the patient and present a virtual object and/or data on the surgical instrument and/or an image of the surgical site in the surgical field of view captured by the camera 79. The AR display 89 may display the AR environment overlaid on a real environment. The display 89 may show a virtual object and/or data, using the AR device 66, such as in a fixed position in the AR environment.

The AR device 66 may include a sensor 90, such as an infrared sensor. The camera 79 or the sensor 90 may be used to detect movement, such as a gesture by a surgeon or other user, that may be interpreted by the processor 85 as attempted or intended interaction by the user with the virtual target. The processor 85 may identify an object in a real environment, such as through processing information received using the camera 79. In other aspects, the sensor 90 may be a tactile, audible, chemical, or thermal sensor to generate corresponding signals that may combined with various data feeds to create the augmented environment. The sensor 90 may include binaural audio sensors (spatial sound), inertial measurement (accelerometer, gyroscope, magnetometer) sensors, environmental sensors, depth camera sensors, hand and eye tracking sensors, and voice command recognition functions.

The AR display 89, for example during a surgical procedure, may present, such as within a surgical field while permitting the surgical field to be viewed through the AR display 89, a virtual feature corresponding to a physical feature hidden by an anatomical aspect of a patient. The virtual feature may have a virtual position or orientation corresponding to a first physical position or orientation of the physical feature. In an example, the virtual position or orientation of the virtual feature may include an offset from the first physical position or orientation of the physical feature. The offset may include a predetermined distance from the augmented reality display, a relative distance from the augmented reality display to the anatomical aspect, or the like.

In one example, the AR device 66 may be an individual AR device. In one aspect, the AR device 66 may be a HoloLens 2 AR device manufactured by Microsoft of Redmond, Wash. This AR device 66 includes a visor with lenses and binaural audio features (spatial sound), inertial measurement (accelerometer, gyroscope, magnetometer), environmental sensors, depth camera, and video camera, hand and eye tracking, and voice command recognition functions. It provides an improved field of view with high resolution by using mirrors to direct waveguides in front of wearer's eyes. Images can be enlarged by changing angles of mirrors. It also provides eye tracking to recognize users and adjust lens widths for specific users.

In another example, the AR device 66 may be a Snapchat Spectacles 3 AR device. This AR device provides the ability to capture paired images and recreate 3D depth mapping, add in virtual effects, and replay 3D videos. The AR device includes two HD cameras to capture 3D photos and videos at 60 fps—while four built-in microphones record immersive, high-fidelity audio. Images from both cameras combine to build out a geometric map of the real world around the user to provide a new sense of depth perception. Photos and videos may be wirelessly synchronized to external display devices.

In yet another example, the AR device 66 may be a Glass 2 AR device by Google. This AR device provides inertial measurement (accelerometer, gyroscope, magnetometer) information overlaid on lens (out of view) to supplement information.

In another example, the AR device 66 may be an Echo Frames AR device by Amazon. This AR device does not have cameras/displays. A microphone and speaker are linked to Alexa. This AR device provides less functionality than a heads-up display.

In yet another example, the AR device 66 may be a Focals AR device by North (Google). This AR device provides notification pusher/smartwatch analog; inertial measurement, screen overlay of information (weather, calendar, messages), voice control (Alexa) integration. This AR device provides basic heads-up display functionality.

In another example, the AR device 66 may be an Nreal AR device. This AR device includes spatial sound, two environmental cameras, a photo camera, IMU (accelerometer, gyroscope), ambient light sensor, proximity sensor functionality. A nebula projects application information on lenses.

In various other examples, the AR device 66 may be any one of the following commercially available AR devices: Magic Leap 1, Epson Moverio, Vuzix Blade AR, ZenFone AR, Microsoft AR glasses prototype, EyeTap to create collinear light to that of the environment directly into the retina. A beam splitter makes the same light seen by the eye available to the computer to process and overlay information, for example. AR visualization systems include HUD, contact lenses, glasses, virtual reality (VR) headsets, virtual retinal display, on in operating room displays, and/or smart contact lenses (bionic lenses).

Multi-user interfaces for the AR device 66 include virtual retinal displays such as raster displays drawn directly on retinas instead of on a screen in front of the eye, smart televisions, smart phones, and/or spatial displays such as Sony spatial display systems.

Other AR technology may include, for example, AR capture devices and software applications, AR creation devices and software applications, and AR cloud devices and software applications. AR capture devices and software applications include, for example, Apple Polycam app, Ubiquity 6 (Mirrorworld using Display.land app)—users can scan and get 3d image of real world (to create 3D model). AR creation devices and software applications include, for example, Adobe Aero, Vuforia, ARToolKit, Google ARCore, Apple ARKit, MAXST, Aurasma, Zappar, Blippar. AR cloud devices and software applications include, for example, Facebook, Google (world geometry, objection recognition, predictive data), Amazon AR Cloud (commerce), Microsoft Azure, Samsung Project Whare, Niantic, Magic Leap.

Situational awareness is the ability of some aspects of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls the modular devices (e.g., a robotic arm and/or robotic surgical tool) that are connected to it and provide contextualized information or suggestions to the surgeon during the course of the surgical procedure.

FIG. 11 illustrates a timeline of a situational awareness surgical procedure. FIG. 11 illustrates a timeline 5200 of an illustrative surgical procedure and the contextual information that a surgical hub 5104 can derive from the data received from the data sources 5126 at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a postoperative recovery room. The situationally aware surgical hub 5104 receives data from the data sources 5126 throughout the course of the surgical procedure, including data generated each time medical personnel utilize a modular device 5102 that is paired with the surgical hub 5104. The surgical hub 5104 can receive this data from the paired modular devices 5102 and other data sources 5126 and continually derive inferences (i.e., contextual information) about the ongoing procedure as new data is received, such as which step of the procedure is being performed at any given time. The situational awareness system of the surgical hub 5104 is able to, for example, record data pertaining to the procedure for generating reports, verify the steps being taken by the medical personnel, provide data or prompts (e.g., via a display screen) that may be pertinent for the particular procedural step, adjust modular devices 5102 based on the context (e.g., activate monitors, adjust the FOV of the medical imaging device, or change the energy level of an ultrasonic surgical instrument or RF electrosurgical instrument), and take any other such action described above.

First 5202, the hospital staff members retrieve the patient's EMR from the hospital's EMR database. Based on select patient data in the EMR, the surgical hub 5104 determines that the procedure to be performed is a thoracic procedure.

Second 5204, the staff members scan the incoming medical supplies for the procedure. The surgical hub 5104 cross-references the scanned supplies with a list of supplies that are utilized in various types of procedures and confirms that the mix of supplies corresponds to a thoracic procedure. Further, the surgical hub 5104 is also able to determine that the procedure is not a wedge procedure (because the incoming supplies either lack certain supplies that are necessary for a thoracic wedge procedure or do not otherwise correspond to a thoracic wedge procedure).

Third 5206, the medical personnel scan the patient band via a scanner 5128 that is communicably connected to the surgical hub 5104. The surgical hub 5104 can then confirm the patient's identity based on the scanned data.

Fourth 5208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices 5102 can automatically pair with the surgical hub 5104 that is located within a particular vicinity of the modular devices 5102 as part of their initialization process. The surgical hub 5104 can then derive contextual information about the surgical procedure by detecting the types of modular devices 5102 that pair with it during this pre-operative or initialization phase. In this particular example, the surgical hub 5104 determines that the surgical procedure is a VATS procedure based on this particular combination of paired modular devices 5102. Based on the combination of the data from the patient's EMR, the list of medical supplies to be used in the procedure, and the type of modular devices 5102 that connect to the hub, the surgical hub 5104 can generally infer the specific procedure that the surgical team will be performing. Once the surgical hub 5104 knows what specific procedure is being performed, the surgical hub 5104 can then retrieve the steps of that procedure from a memory or from the cloud and then cross-reference the data it subsequently receives from the connected data sources 5126 (e.g., modular devices 5102 and patient monitoring devices 5124) to infer what step of the surgical procedure the surgical team is performing.

Fifth 5210, the staff members attach the EKG electrodes and other patient monitoring devices 5124 to the patient. The EKG electrodes and other patient monitoring devices 5124 are able to pair with the surgical hub 5104. As the surgical hub 5104 begins receiving data from the patient monitoring devices 5124, the surgical hub 5104 thus confirms that the patient is in the operating theater.

Sixth 5212, the medical personnel induce anesthesia in the patient. The surgical hub 5104 can infer that the patient is under anesthesia based on data from the modular devices 5102 and/or patient monitoring devices 5124, including EKG data, blood pressure data, ventilator data, or combinations. Upon completion of the sixth step 5212, the pre-operative portion of the lung segmentectomy procedure is completed and the operative portion begins.

Seventh 5214, the patient's lung that is being operated on is collapsed (while ventilation is switched to the contralateral lung). The surgical hub 5104 can infer from the ventilator data that the patient's lung has been collapsed. The surgical hub 5104 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth 5216, the medical imaging device 5108 (e.g., a scope) is inserted and video from the medical imaging device is initiated. The surgical hub 5104 receives the medical imaging device data (i.e., still image data or live streamed video in real time) through its connection to the medical imaging device. Upon receipt of the medical imaging device data, the surgical hub 5104 can determine that the laparoscopic portion of the surgical procedure has commenced. Further, the surgical hub 5104 can determine that the particular procedure being performed is a segmentectomy, as opposed to a lobectomy (note that a wedge procedure has already been discounted by the surgical hub 5104 based on data received at the second step S204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 5104), and monitoring the types of visualization devices utilized.

For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device 5108, the surgical hub 5104 can thereby determine the specific type of surgical procedure being performed and/or the technique being used for a particular type of surgical procedure.

Ninth 5218, the surgical team begins the dissection step of the procedure. The surgical hub 5104 can infer that the surgeon is in the process of dissecting to mobilize the patient's lung because it receives data from the RF or ultrasonic generator indicating that an energy instrument is being fired. The surgical hub 5104 can cross-reference the received data with the retrieved steps of the surgical procedure to determine that an energy instrument being fired at this point in the process (i.e., after the completion of the previously discussed steps of the procedure) corresponds to the dissection step.

Tenth 5220, the surgical team proceeds to the ligation step of the procedure. The surgical hub 5104 can infer that the surgeon is ligating arteries and veins because it receives data from the surgical stapling and cutting instrument indicating that the instrument is being fired. Similarly to the prior step, the surgical hub 5104 can derive this inference by cross-referencing the receipt of data from the surgical stapling and cutting instrument with the retrieved steps in the process.

Eleventh 5222, the segmentectomy portion of the procedure is performed. The surgical hub 5104 infers that the surgeon is transecting the parenchyma based on data from the surgical instrument, including data from a staple cartridge. The cartridge data may correspond to size or type of staple being fired by the instrument. The cartridge data can indicate the type of tissue being stapled and/or transected for different types of staples utilized in different types of tissues. The type of staple being fired is utilized for parenchyma or other tissue types to allow the surgical hub 5104 to infer that the segmentectomy procedure is being performed.

Twelfth 5224, the node dissection step is then performed. The surgical hub 5104 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 5104 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Upon completion of the twelfth step 5224, the incisions and closed up and the post-operative portion of the procedure begins.

Thirteenth 5226, the patient's anesthesia is reversed. The surgical hub 5104 can infer that the patient is emerging from the anesthesia based on the ventilator data (i.e., the patient's breathing rate begins increasing), for example.

Lastly, fourteenth 5228, the medical personnel remove the various patient monitoring devices 5124 from the patient. The surgical hub 5104 can thus infer that the patient is being transferred to a recovery room when the hub loses EKG, BP, and other data from the patient monitoring devices 5124. The surgical hub 5104 can determine or infer when each step of a given surgical procedure is taking place according to data received from the various data sources 5126 that are communicably coupled to the surgical hub 5104.

In addition to utilizing the patient data from EMR database(s) to infer the type of surgical procedure that is to be performed, as illustrated in the first step 5202 of the timeline 5200 depicted in FIG. 11, the patient data can also be utilized by a situationally aware surgical hub 5104 to generate control adjustments for the paired modular devices 5102.

Surgical displays (e.g. displays 7, 9, 19, 35, 62, 65, 66, 67, and 89) play an important function within the operating room, by provide useful information to a clinician (e.g. surgeon, surgical staff) that can used to, among other things, assess the progress of a surgical procedure, determine subsequent steps to take in the surgical procedure, monitor patent vital signs, etc. The displays need to be large enough such that this information being provided can be seen, yet not so large as to be overbearing and obstruct workflow or movement in a crowded operating room.

For example, an imaging device, such as one of the many imaging devices described elsewhere herein, is used to capture a livestream of a surgical field during a surgical procedure. A display shows this livestream captured by the imaging device such that the clinician can view the surgical field during the surgical procedure.

During the course of the surgical procedure, information that is relevant to or associated with the surgical procedure can be overlaid onto the livestream on the display. For example, an electrocardiogram (EKG) monitors a patient's heart rate during the surgical procedure and the monitored heart rate is overlaid on the livestream such that the clinician can ensure that the patient is stable.

Various other sensors, detectors, modules, etc. monitor other parameters over the course of the surgical procedure and information associated with these parameters can also be overlaid onto the display. However, some overlaid information may be of more significance than other overlaid information. As an example, when a clinician is manipulating tissue with an end effector of a surgical instrument, information regarding how much force is being applied to the tissue with the end effector is relevant to monitor so as to ensure the tissue isn't being unintentionally damaged.

However, owing the amount of information being overlaid on the display, more important information, such as a force being applied to the tissue, may be overlooked or missed by the clinician. This abundance of competing information can cause the surgeon to become overwhelmed with information that may be detrimental to their ability to adequately perform the surgical procedure, which can prove costly to the patient. Accordingly, there is a need to prioritize, control and/or limit the amount of data/information that is being overlaid on the display.

Figure 12:
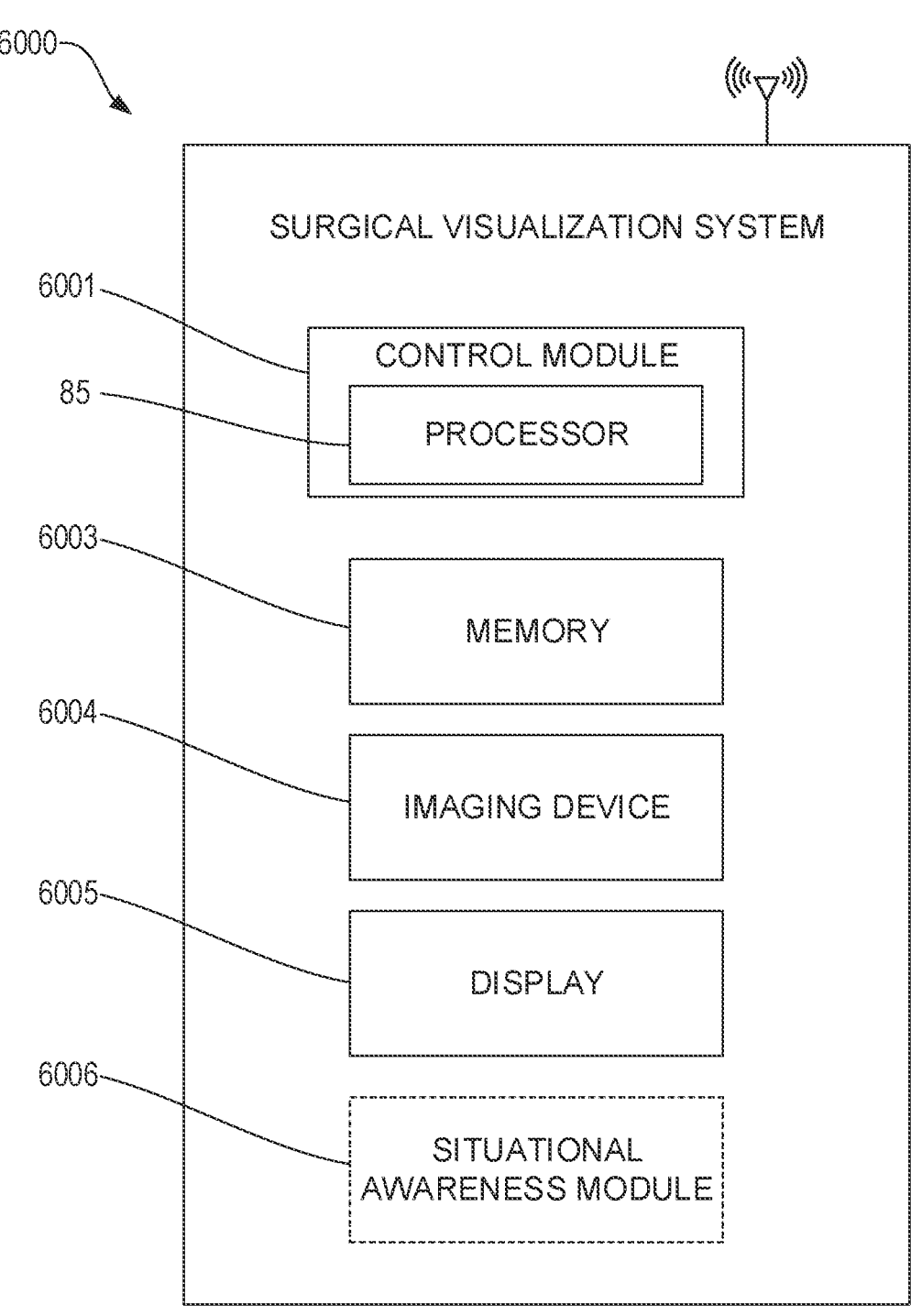
FIG. 12 illustrates a surgical visualization system, in accordance with at least one aspect of this disclosure.

FIG. 12 illustrates a surgical visualization system 6000, in accordance with at least one aspect of this disclosure. Various components of the surgical visualization system 6000 are similar in many respect to components of other systems described elsewhere in the present disclosure and, as such, are not repeated herein at the same level of detail for brevity. The surgical visualization system 6000 includes a control module 6001 configured to perform various techniques described herein, for example, by using one or more processors or processing circuitry such as the processor 85. In some implementations, the system 6000 can include, be used in conjunction with, or be communication with the augmented reality device 85, for example. The system 6000 may further include storage medium such as, for example, a memory 6003, an imaging device 6004 such as, for example, the camera 88, and a display 6005. The system 6000 may further include one or more speakers 91, haptic controllers 92, and/or sensors 90 (see FIG. 10). The display 6005 can include, for example, the AR display 89, a VR display, a projector, a heads-up display, a screen, and/or any other suitable device for portraying visual content.

In some implementations, the system 6000 is incorporated into the computer-implemented interactive surgical system 50, for example. In some implementations the system 6000 is in operable communication with one or more hubs, systems, networks, servers, and/or databases that can deliver surgical data to the system 6000. For example, the system 6000 can be in operable communication with cloud 54 that may include a remote server 63, robot hub 72, surgical hub 56, devices/instruments 21, and/or modular control tower 23 via wired or wireless communication standards or protocols, as described herein. In some implementations, the system 6000 includes a situational awareness module 6006 similar to that described in connection was the surgical hub 5104. The situational awareness module 6006 can be trained to extrapolate contextual information about a surgical procedure based on a multitude of perioperative data received through sensor input and/or user input.

In view of the foregoing problems associated with competing amounts of information to be overlaid on a display, the present disclosure provides a system, such as system 6000, that can monitor, sense, and/or detect the occurrence of triggering events that occur before, during, or after a surgical procedure so as to control the information that is overlaid on the display. In one aspect, triggering events can be events detected by the system, via any number of sensors, systems, or module described elsewhere herein, that can initiate changes in the information that is overlaid on the display. In various embodiments, detection of a triggering event can cause information to be added to the display, removed from the display, or adjusted on the display, such as moving the information to a different position on the display or adjusting a size that the information occupies on the display, as examples, and will be described in greater detail elsewhere herein.

In one aspect, the system can detect recognition based triggers, via a surgical visualization system, such as visualization system 8, and update overlaid information on the display accordingly. In various embodiments, the visualization system 8 can be similar to visualization systems described in U.S. Pat. No. 11,000,270, U.S. Patent Application Publication No. 2020/0015900, U.S. Patent Application Publication No. 2020/0015899, U.S. Pat. No. 11,259, 793, U.S. Patent Application Publication No. 2020/0015924, U.S. Patent Application Publication No. 2020/0015898, U.S. Patent Application Publication No. 2020/0015906, U.S. Patent Application Publication No. 2020/0015907, U.S. Pat. No. 10,925,598, U.S. Patent Application Publication No. 2020/0015914, and U.S. Patent Application Publication No. 2020/0015902, which are hereby incorporated by reference in their entireties herein.

In one aspect, recognition based triggers can be, for example, objects (surgical instruments, surgical implants, surgical structures, organs, tissue, etc.) with predefined and/or identifiable sizes, shapes, patterns, colors, arrangements, or any other identifiable features that are unique to the object. In various embodiments, the system can include a memory, such as memory 6003, that stores data associated with the object therein, such as images and/or parameters associated with the objects, for comparison against objects that are captured by an imaging device, such as imaging device 6004, during a surgical procedure. In one aspect, the memory can store two-dimensional images of the objects therein, such as top views, bottom views, side views, isometric views, or any other suitable two-dimensional view of the object, as examples. In one aspect, the memory can store three-dimension models, such as CAD models, of the objects therein so that any number of image views are available to the system for comparison. In one aspect, the three-dimensional models can be generated using pre-operative imaging techniques, such as CT scans or MRI scans, using visualization system 8.

In one example embodiment, the system can identify, via the imaging device, an object in a livestream. The system can compare an image of the object and parameters thereof (color, dimensions, etc.) that can be identified by the system to the images and parameters stored in the memory to determine if the object is a known object. In the event of a match, or at least a substantial match, the system can overlay information on the display associated with the object identified in the livestream.

In one example embodiment, the imaging device can capture a natural surface feature, such as the incisura angularis of the stomach, in a livestream. The system can transmit a visual representation of the livestream to a display such that the natural surface feature can be seen by the surgical staff. The system can further compare the image and determined parameters of the natural surface feature to images and parameters stored in the memory to determine if the natural surface feature is a known natural surface feature. In the event of a positive identification of the natural surface feature, the system can overlay information on the display associated with the natural surface feature. In one aspect, the information associated with the natural surface feature can be stored in the memory. In one aspect, the overlaid information can be overlaid on top of the natural surface feature on the display. In one aspect, the overlaid information can be overlaid near the natural surface feature on the display such that the overlaid information is readily seen, but does not obstruct the view of the natural surface feature on the display. In one aspect, the overlaid information can be overlaid in a predetermined location on the display designated for positive identifications in the livestream, such as a corner of the display.

In one aspect, as described above, the object in the livestream can be a natural surface feature. In one aspect, the object in the livestream can be a surface feature of a surgical instrument, such as a surgical staple cartridge. In one aspect, the object in the livestream can be a marker, such as a barcode, an emblem, a pattern, or the like. In one aspect, the object in the livestream can be any number of objects that the system can compare to images and parameters of the objects stored in the memory.

In one aspect, the system can overlay information on the display based on a partial identification on an object in the livestream. In one aspect, the system can identify objects in the livestream that meet a threshold acceptance limit and overlay information on the display if the threshold acceptance limit is reached or exceeded. In one aspect, the threshold acceptance limit can be predefined, stored in a memory, user defined, based on industry standards, or combinations thereof. In the event that the threshold acceptance limit is not reached, the system can not overlay information on the display.

In one example embodiment, the system can identify a portion of a staple cartridge in the livestream. In one aspect, the staple cartridge could be obstructed, or partially out of frame, on the livestream, such that only the portion of the staple cartridge is visible. The system can compare the viewable portion of the staple cartridge to images and parameters of staple cartridges stored in the memory. In one aspect, parameters of the staple cartridge can be color of the cartridge, viewable/identifiable dimensions of the cartridge, such as distance between staple cavities or the length of the elongate slot that the cutting knife traverses, the number of staple cavities, or any other identifiable parameter associated with the staple cartridge. In the event the system determines that that the portion of the staple cartridge reaches or exceeds a threshold acceptance limit compared to a surgical staple cartridge stored in the memory, as will be described in more detail below, the system can overlay information on the display based on the determination.

In some embodiments, a threshold acceptance limit can be defined as a percentage of the image or parameters thereof stored in the memory that has been identified in the livestream. In one example embodiment, the system can identify a portion of a staple cartridge in the livestream. The system can analyze the image and determine that 75% of a staple cartridge stored in the memory has been identified on the object from the livestream. In one embodiment, the system can have, for example, a threshold acceptance limit of 50%, which has been exceeded by the comparison between the object in the livestream and the images stored in memory. Accordingly, information associated with the staple cartridge can be overlaid on the display. In various embodiments, the threshold acceptance limit can be stored in a memory, be user defined, vary from user to user, be based on standard industry practices, or combinations thereof.

In some embodiments, the threshold acceptance limit can be defined as a threshold number of parameters that have been identified based on a comparison of the object identified in the livestream and an object stored in the memory. In one example embodiment, the system can identify a portion of a staple cartridge in a livestream. The system can identify various parameters of the staple cartridge, such as the color, the spacing between staple cavities, known marks thereon, or any other identifiable feature of the staple cartridge. The system can identify these parameters and compare the same to parameters stored in the memory, such as parameters stored in a look-up table. In one aspect, the threshold acceptance limit can be set to 3 matches between the object identified in the livestream and an object stored in the memory. In the event that the system determines that the threshold acceptance limit has been reached or exceeds (such as identifying the color of the staple cartridge, identifying the staple cavity spacing, viewing a known emblem thereon, as an example), the system can overlay information on the display according to the match. In various embodiments, the threshold acceptance limit can be a combination of a percentage of an object identified in the livestream and a number of parameters of the object that have been identified. In one example embodiment, the threshold acceptance limit can be 50% of the object in the livestream matching an object stored in the memory and 3 parameters matching the object stored in the memory.

In one aspect, the system can overlay a confidence level associated with the identified match. As described herein above, the system can identify partial matches in the livestream and overlay information when a threshold acceptance limit has been reached or exceeded. In the event of a partial match, the system can overlay a confidence level, or percentage, with the overlaid information. In one example embodiment, a staple cartridge stored in a memory can have 8 parameters associated therewith, but the threshold acceptance limit is set to only 3 matches. In the event that the system identifies 3 positive matches of the 8 parameters in the staple cartridge in the livestream, the system can overlay information about the staple cartridge on the livestream. In addition, the system can overlay a note identifying that the overlay is based on 3 of 8 parameters being identified, i.e., not a complete match. By overlaying a confidence level, surgical personnel viewing the display can utilize their own judgement on whether or not they agree with the determination. In various embodiments, the system can include a user interface that allows the surgical staff to accept or decline the overlaid information, thereby giving the staff the ability to remove the overlaid information if they disagree with the assessment or do not require the overlaid information.

In various embodiments, the system can overlay information on the livestream according to the identified object on the livestream. In one aspect, the system can overlay markers identifying various regions or features of the object based on a positive identification. In one example embodiment, when the system identifies the object as being the stomach, the system can overlay markers pointing to the greater curvature, the lesser curvature, the incisura angularis, as examples. In one aspect, the system can overlay a segmented overlay on the object identifying various regions of the object. In one example embodiment, the system can identify the stomach and overlay a segmented overlay that identifies the fundus, the body, the pyloric antrum, the pyloric canal, and the duodenum, as examples.

In one aspect, the system can overlay directional information on the livestream based on a positive identification. In one example embodiment, in the event the system identifies the incisura angularis, the system can overlay directional arrows that assist a surgeon in finding other areas of the stomach, such as the greater curvature, or other organs in the patient, such as the intestines. In one aspect, the directional arrows can be based on both the identified object, as well as the orientation or angle, at which the object was identified. In some aspects, the directional arrows can be based on a determined step of the surgical procedure. In one example embodiment, in the event the current step of the surgical procedure requires the surgeon to be looking at the greater curvature, but the surgeon is currently looking at the incisura angularis, the system can overlay a directional arrow indicating what direction the surgeon need go in order to reach the greater curvature.

In one aspect, the system can overlay information regarding known parameters or features of the object. In one example embodiment, the system can identify a green surgical staple cartridge in the livestream. In the event of a positive identification, the system can overlay parameters on the livestream associated with the identified staple cartridge, such as the size of the staples, the staple material, the tissue thickness intended for use with the identified staple cartridge, and combinations thereof, as examples.

In one aspect, the system can overlay information on the display according to an identified orientation of the object identified in the livestream. In one example embodiment, the system can identify an object in the display, based on a comparison of the object to data associated with objects stored in the memory. In one embodiment, the system can identify that the object is being viewed at a first orientation, such as a side view of the object, and trigger a first overlay adjustment. In another embodiment, the system can identify that the object is being viewed at a second orientation, such as a top view of the object, and trigger a second overlay adjustment that is different than the first overlay adjustment. In one embodiment, the system can identify that the object is being viewed at a first orientation, such as at a 30 degree angle relative to an upright position thereof, and trigger a first overlay adjustment. In another embodiment, the system can identify that the object is being viewed at a second orientation, such as at a 15 degree angle relative to an upright position thereof, and trigger a second overlay adjustment that is different than the first overlay adjustment.

In one aspect, the system can include interactive sensors and the triggering event can be a user interacting with the interactive sensor. In various embodiments, the interactive sensor can be an audible sensor and the triggering event can be the system identifying, via the audible sensor, a known sound, word, phrase, or the like, that can be stored in the memory. In one example embodiment, a surgeon can say "re-focus" and the system can detect the word, via the audible sensor, and update the overlaid information on the display based on the identified word. In various embodiments, the triggering event can be based on predefined movements captured by the imaging device. In one aspect, the predefined movements can be stored in a memory and compared to movements captured by the imaging device. In one example embodiment, the surgeon can move an end effector of a surgical instrument in a circular motion, the system can detect the circular motion in the livestream, and update the overlaid information on the display, based on the detected motion. In various embodiments, the adjustment that the system makes to the overlaid information according to the detected interaction can be stored in the memory. In one example embodiment, a surgeon can say "clear" and the system can determine, based on data stored in the memory, that "clear" means that the surgeon wants all overlaid information on the display to be removed.

In some aspects, the adjustment that the system makes to the overlaid information according to the detected interaction can be based on an identified step of the surgical procedure. In various embodiment, a situational awareness module, such as situational awareness module 6006, can determine a step of the surgical procedure being performed, based on one or more inputs received by the system. Based on the interaction provided by the user and the determined step of the surgical procedure, the system can adjust the overlaid information on the display accordingly. In one example embodiment, the surgeon can provide an audible command, such as a sound, to the system. The system, via the situational awareness module, can determine that a particular step of a surgical procedure is being performed. The system can compare the sound to sounds stored in the memory. In one aspect, the memory can store various executable instructions to perform based on both the detected sound and the determined step of the surgical procedure. In one aspect, a certain sound can cause a first adjustment to the overlaid information for one determined step and a second adjustment to the overlaid information for a second determined step, where the first and second adjustments are different. In various embodiment, an audible command can cause the same adjustment to the overlaid information independent of the determined step of the surgical procedure.

In one aspect, the system can detect location based triggers that cause overlaid information on the display to be adjusted. In various embodiments, the system can include various sensors and visualization systems, such as those described elsewhere herein, that can track and/or determine positions of various components and/or individuals associated with the surgical procedure. In one aspect, the system can utilize GPS for determining positions of various components and/or individuals. In one aspect, the system can include a digital compass for determining positions of various components and/or individuals. In one aspect, the system can include sensors for measuring velocity data and acceleration data (such as an accelerometer, as an example) for determining positions of various components and/or individuals. In one aspect, the components and individuals for tracking can include position sensors that are capable of being tracked by the system. The above-provided position tracking techniques can be used alone and in combination with each other for the purposes of identifying positions of components and/or individuals within or outside of the OR.

In one example embodiment, a surgeon can be working thru a colorectal sigmoidectomy mobilization using a surgical cutting device and viewing a livestream thereof on a display. The system can detect, via any number of position tracking techniques, as referenced above, when the end effector of the surgical cutting device is approaching the transection point of the blood supply. Based on the system detecting that the end effector is approaching, or has reached, the transection point, the system can adjust the display to overlay information to aid in the upcoming step of the mobilization. As one example, the system can overlay the location and directionality of the blood flow and to where the blood feeds based on inputs from a surgical visualization system to the system, thereby aiding in the visualization of the next step of the procedure.

In various embodiments, the system can detect, via any number of position tracking techniques, as referenced above, a position of an individual, or a group of individuals, within or outside of the OR and adjust the overlaid information on the display based on their detected position(s). In one aspect, the system can monitor a position of an individual, such as a nurse, within the hospital, that has a display, such as a wearable AR device 66, as an example. Although the proceeding discussion will be in the context of the wearable AR device, it should be understood that any other display described herein can be used in the alternative to achieve the same results. In various embodiments, instead of an AR device 66, the nurse could have a tablet, a cell phone, or any other portable display, as examples.

In various embodiments, the system can detect the position of the individual with the portable device relative to any number of locations. In one aspect, the system can detect when the individual is approaching, or has arrived, at a location, and adjust the information overlaid on the AR device 66 accordingly. In one example embodiment, when the nurse wearing the AR device 66 arrives at a location, such at the door of a stock room, the system can overlay information on the lens of the AR device associated with the stock room. In one embodiment, the system can overlay what room is behind the door. In one embodiment, the system can overlay what surgical equipment is stored in the stock room. In one embodiment, the system can overlay if the stock room includes required equipment for a surgical procedure, based on a detected step of the surgical procedure by the system. In various embodiments, the system can overlay any amount of information useful to the individual for retrieving desired pieces of equipment for a surgical procedure. In one aspect, the system can overlay information based on a detected step of a surgical procedure, such as directional information indicating where certain pieces of equipment can be obtained for completing the step of the surgical procedure. In various embodiments, the system can overlay information based on a user input, such as a verbal command, inquiring if a certain piece of equipment can be found at the identified location. Information regarding locations, such as what equipment can be found at the locations, can be stored in a memory.

In various embodiments, the system can determine steps of a surgical procedure that are being performed, or are soon to be performed, and adjust the overlaid information on the AR device according to the determination. In one example embodiment, the system can determine, via the situational awareness module, that a surgical stapling step is soon to be performed and a particular type of staple cartridge will be required. The system can overlay, on a nurse's AR device, as an example, that the particular type of staple cartridge will soon be needed. The system can further overlay on the AR device, for example, where the staple cartridge can be found, what the staple cartridge looks like, a model number of the staple cartridge, or any other suitable identifying information that would aid the nurse in acquiring the staple cartridge. The system can further overlay, on the AR device, directional information to aid the nurse in finding the staple cartridge. In one example embodiment, the system can overlay information as to where the staple cartridge can be found, such as a room number, a shelf number, a bin number, or any other suitable descriptive information as to where the staple cartridge can be found. In one example embodiment, the system can utilize position tracking techniques, such as GPS, and overlay directional arrows on the lens of the AR device to visually direct the nurse to where the staple cartridge can be retrieved. In one aspect, the system can overlay highlights on key features to aid in retrieving the staple cartridge. In one example embodiment, when the door of the stock room that the staple cartridge is stored in comes into the field of view of the AR device, the system can highlight the door to inform the nurse that the staple cartridge can be found behind the highlighted door. Any combination of the above-referenced embodiments can be used in combination with each other to aid in identifying a location of desired equipment.

In various other embodiments, the AR device can adjust the overlaid information based on the surgical procedure, the determined surgical steps of the surgical procedure, the surgeon's preferences, user inputs, such as physical or verbal inputs, or combinations thereof. In one example embodiment, when a nurse enters a stock room wearing the AR device, the system can adjust the overlaid information to point to, or highlight, pieces of equipment based on the surgical procedure, the determined surgical steps of the surgical procedure, the surgeons preferences, user inputs, such as physical or verbal, or combinations thereof. In one aspect, the system can adjust the overlaid information to highlight pieces of equipment in the stock room that are currently missing from the OR that are needed, or will be needed, for the surgical procedure. In one aspect, the system can adjust the overlaid information based a verbal request from the nurse inquiring on where a particular piece of equipment is located. Based on the request, the system can adjust the overlaid information accordingly. In one aspect, the system can highlight the requested item brighter, or more intensely, than the other highlighted items in the stock room. In another example embodiment, the system could unhighlight everything except for the requested piece of equipment.

In various embodiments, the system can track the location of the AR device and change the relevance of triggering events based on the location thereof. In one aspect, a first user can be wearing a first AR device and be at a first location and a second user can be wearing a second AR device and be at a second location. In one example embodiment, a triggering event can be detected that would cause the system to adjust the overlaid information. The system can detect that the first user is associated with the triggering event and that the second user is unassociated with the triggering event. In one aspect, the system can detect that the first user is within a certain distance at which the triggering event occurred and the second user is outside the certain distance at which the triggering event occurred. Based on the determination, the system can update the overlaid information of the first AR device, but not on the second AR device. In one example embodiment, a surgeon can be performing a surgical procedure wearing an AR device and a nurse can be retrieving a piece of equipment wearing an AR device. When the nurse arrives at the stock room (location based triggering event), the system can adjust information overlaid on the nurses AR device, while maintaining what is overlaid on the surgeons AR device. This selective adjustment in overlaid information prevents displays from being adjusted where the overlaid information may be of little or no value to particular individuals.

In various embodiments, the system can adjust information overlaid on the display based on any number of triggering events as detected by a visualization system, such as any number of the visualization systems described here. In one aspect, the system can adjust the overlaid information based on a determination of who is holding a particular surgical device. In one aspect, the system can adjust the overlaid information based on a particular surgical device coming into the field of view of the visualization system. In one aspect, the system can adjust the overlaid information based where a surgical device is relative to the patient. In one example embodiment, when a particular surgical device comes within a threshold distance of a patient, as determined by any number of inputs, such as the visualization system, position sensors, or any other position tracking techniques described herein, the system can adjust the display to overlay information related to the surgical device. In one example embodiment, when a particular surgical device exits a threshold distance of a patient, as determined by any number of inputs, such as the visualization system, position sensors, or any other position tracking techniques described herein, the system can adjust the display to remove overlaid information related to the surgical device. In one example embodiment, when a particular surgical device reaches a threshold distance of a patient, as determined by any number of inputs, such as the visualization system, position sensors, or any other position tracking techniques described herein, the system can adjust the display to add overlaid information related to the surgical device.

In various embodiments, the system can adjust information overlaid on the display based on determined prioritizations for surgical tasks. In one aspect, the system can determine a step of the surgical procedure, using for example, a situational awareness module, and adjust the importance, or the occurrence, of triggering events based on the determination. In one example embodiment, the system can determine, using the situational awareness module, that a surgical stapling step is being performed, or is to be performed. The system can monitor triggering events during the surgical stapling step and determine if adjustments to the overlaid information are required according to their determined relevance with the surgical stapling step. In one aspect, a triggering event, such as excess force being applied to the tissue being stapled, can be detected. The system can determine that the excess force is relevant to the current step of the surgical procedure and update overlaid information on the display accordingly. In one aspect, a triggering event, such as temperature of the tissue exceeding a temperature threshold, can be detected. The system can determine that the excess temperature is less relevant to the current step of the surgical procedure and can choose to not update the overlaid information based on the determination. In various embodiments, relevance of triggering events for steps of a surgical procedure can be stored in a memory, be used defined, be based on industry standards, or a combination thereof. In one aspect, when the system determines that information is less relevant to the current step of the surgical proceed, the system can overlay the information on the display, but adjust how much of the display the information overlays. In one example, when the system detects a triggering event that is less relevant the surgical step currently being performed. The system can overlay information associated with the step on the display, but overlay the information 50% of the size at which the overlaid information would normally occupy. In other embodiments, the system can overlay information associated with the step on the display, but position the information at a less readily visible portion of the display, such as in a corner or on an edge of the display.

In various embodiments, the system can adjust information overlaid on the display based on the criticality of the data to a user that is operating a surgical device. In one embodiment, the surgeon can utilize a surgical stapler to staple tissue. The system can detect excess force applied to the tissue, which the system deems critical, based on data stored in a memory, and adjust a display associated with the surgeon, such as an AR device 66, such that the excess force detection is made known to the surgeon utilizing the surgical stapler.

In various embodiments, the system can adjust information overlaid on the display based on the detection of a certain type of surgical device being used by a user. In one aspect, the system can adjust the overlaid information to inform the user of issues related to the particular surgical device being used so that the user can proceed knowing the potential failure points. As one example, the system can adjust the overlaid information to inform the user of how potential misuse of the surgical device can cause secondary failures, such as failures to other surgical devices. In various embodiments, this data can be stored in a memory. In various embodiments, this data can be accessible from a cloud-based system, such as cloud-based system 4.

In various embodiments, the system can adjust information overlaid on the display by moving information from a first display to a second display. In one aspect, the system can detect the occurrence of a triggering event that can cause a change in the overlaid information on a primary display in the OR. In various embodiments, this change in the overlaid information can be changing a size of a portion of the information, a weight of a portion of the information, a position of a portion of the information, removing overlaid information, adding overlaid information or combinations thereof. In one aspect, as a result of the adjustment, the system can move information deemed less relevant, such as less relevant to a particular surgical step being performed, from the first display to a second display, thereby keeping the information available to the surgical staff, but on a display that may not be the primary focus on the surgical staff.

In various embodiments, the system can adjust information overlaid on the display based on a detection that a triggering event was induced by a surgical instrument utilized by a particular user. In some aspects, the system can determine what surgical devices are actively being used by what surgical personnel based on data received from sensors, modules, and/or visualization systems within the OR. In one example embodiment, the system can determine an energy device is actively being used based on data received from the generator module 40. In one example embodiment, the system can determine a surgical device is actively being used based on data received from the sensor module 29. In one example embodiment, the system can determine a surgical device is actively being used based on data received from an imaging module 25, or any number of visualization systems described elsewhere herein. In one example embodiment, the system can determine a surgical device is actively being used based on inferences made from the situational awareness module. In one example embodiment, the system can determine that a device is actively being used based on the system receiving a signal indicative of a pairing occurring between a user-worn identifier and a surgical instrument, as explained in U.S. Pat. No. 10,758,310, which is hereby incorporated by reference in its entirety herein. In various embodiments, the system can determine what surgical devices are being actively used based on various sensors, modules, and input devices described herein, alone or in combination with each other.

In various embodiments, the system can detect triggering events that originate from surgical instruments actively controlled by a user and update the overlaid information on the display accordingly. In one example embodiment, the system can detect that a surgeon is actively using a tissue manipulator to manipulate tissue at a surgical location. The system can detect a tissue tension that exceeds a tissue tension threshold and determine that the tension was induced by the tissue manipulator associated with the surgeon. Based on the detected event and instrument origination, the system can adjust the overlaid information on the display, such as a wearable AR device worn by the surgeon.

In various embodiments, the system can detect triggering events that originate from outside of an active surgical instrument controlled by a user and update the overlaid information on the display accordingly. In one example embodiment, a liver retractor that is unassociated with a surgeon can be deployed and fixated to the liver while the surgeon is actively using two instruments for dissection of the liver. Based on the interaction of the two actively used instruments by the surgeon, a tissue tension in the liver can be induced due to the fixated retractor that exceeds a tension threshold. The system can detect the induced tissue tension by the retractor, such as using a visualization system, and adjust the overlaid information on the display, such as an AR device worn by the surgeon, despite the tissue tension event being induced by a component that is unassociated with the surgeon. Accordingly, the system can update the information on the AR device according to events that are induced by instruments, or actions, associated with or unassociated with a particular user.

In various embodiments, the system can adjust information overlaid on the display based on the detection of a risk event. In one aspect, a risk event can be an event that has at least some likelihood of causing an outcome that is unfavorable with regard to the surgical procedure. In one example embodiment, the risk event can be a detection of a particular type of device being used for a particular step of a surgical procedure. In another example embodiment, the risk event can be the end effector of a surgical instrument coming within a threshold distance of a critical structure, such as an artery, a vein, or a tumor, as examples, within the patient. In one example embodiment, the risk event can be the system detecting that a certain staple cartridge has been installed in a stapling device that is improper for the determined step of the surgical procedure. In some embodiments, the risk event can be an end effector of a surgical instrument articulating too far from an intended position. In any aspect, a detection of a risk event can cause the system to overlay a warning, or a corrective step, on the display explaining the detected risk event and possible remedies to avoid the risk event.

In various embodiments, the system can adjust information overlaid on the display based on the detection of an event that originates from outside of the field of view. In one aspect, an imaging device can capture a livestream of a surgical field and transmit the livestream to a display for the surgical staff to view. An event can be induced, or originate, from outside of the livestream of the surgical field, that would require the attention, or reaction, or a surgeon. In one example embodiment, a surgeon can be manipulating tissue that is visible in the surgical field on the display. As a result of the tissue manipulation, a portion of the tissue outside of the surgical field could tear as a result of a threshold tension being inadvertently applied to the tissue. The system can detect the tear, via, for example, a visualization system, and alert the surgeon that the tissue tear has occurred outside of the surgeon's field of view. This allows the surgeon to reposition the imaging device to the location of the tear and take appropriate action. In one aspect, the system can overlay directional information informing the surgeon where to look to find the event that originated outside of the field of view.

In various embodiments, the system can detect a triggering event that can cause an adjustment to the overlaid information on a wearable display. In some aspects, in addition to adjusting the overlaid information on the wearable display, the system can also adjust the overlaid information on various other displays in the OR such that individuals not wearing wearable AR devices can also view the adjusted overlays. In one example embodiment, the system can detect a triggering event that causes overlaid information on an AR device to be adjusted. In addition, the system can adjust the overlaid information on other displays in the OR, such as display 19, for surgical personnel not wearing AR devices 66 to view.

In various embodiments, the system can adjust the overlaid information on the display in any number of ways. In one example embodiment, upon occurrence of a triggering event, the system can overlay information regarding the state of a device accordingly to any number of sensors. In one example embodiment, upon occurrence of a triggering event, the system can overlay information regarding the heat or thermal profile of a device, which could be detected by temperature sensors. In one example embodiment, upon occurrence of a triggering event, the system can overlay information regarding a direction in which the imaging device should be moved to adjust the surgical field of view thereof. In one example embodiment, upon occurrence of a triggering event, the system can overlay information regarding danger areas, such as areas of tissue that should be avoided in order to avoid potential damage to the patient. In one example embodiment, upon occurrence of a triggering event, the system can overlay information regarding a state of the tissue as determined by any number of sensors. In one example embodiment, upon occurrence of a triggering event, the system can overlay information regarding external implants detected by the system, such as clips or staples implanted in a patient.

In various embodiments, the system can detect the occurrence of a packaging housing a surgical component being opened and adjust overlaid information on the display accordingly. In one example embodiment, the system can detect a packaging being opened that includes a surgical staple cartridge reload. The system can overlay information associated with the component within the packaging, such as implications for secondary packaging, such as staple retainers. In some aspects, the system can overlay information on the display such as a parameters associated with the component that is within the package, such as staple size, staple material, or intended tissue thickness to be stapled with the cartridge, as examples.

In various embodiments, the system can detect a surgical step of a surgical procedure and adjust the overlaid information accordingly. In one aspect, the system can detect a surgical step that subsequently requires a disposal step, such as disposing of an old surgical staple cartridge in an instrument and replacing the instrument with a new cartridge. In one example embodiment, the system can detect the completion of a stapling stroke and overlay instructions to the surgical staff that the cartridge needs to be removed and replaced. In one aspect, the overlaid information can further identify the type of replacement cartridge to utilize to complete the subsequent staple firing stroke. In various embodiments, the system can overlay information regarding where the surgical staple cartridge can be disposed.

In various embodiments, the system can adjust overlaid information based on monitored parameters associated with a patient reaching or exceeding a parameter threshold. In one aspect, any number of sensors or systems can monitor parameters associated with a patient, such as heart rate, and adjust the overlaid information accordingly. In one aspect, the system can monitor a value of various parameters and compare the values to parameters thresholds that are stored in a memory. In the event the value of the parameter reaches or exceeds a parameter threshold, the system can adjust the overlaid information to information the user of the occurrence of the threshold being reached or exceeded such that subsequent action can be taken. In some embodiments, the system can overlay corrective actions on the display that can aid in dropping the value of the parameter below the parameter threshold. In various embodiments, the system can monitor a rate of change of a parameter associated with a patient and adjust the overlaid information based on the rate of change reaching or exceeding a rate of change threshold.

In various embodiments, the system can detect an occurrence of a triggering event by detecting an accumulation of partial triggering events and comparing the accumulated events to a triggering event threshold. In one aspect, the system can set a triggering event count and count the number of occurrences of partial triggering events. In one example embodiment, the system can set the triggering event count to 0 at the start of a surgical procedure. In another example embodiment, the system can set the triggering event count to 0 at the start of a particular step of a surgical procedure. In one aspect, the system can rest the triggering event count back to 0 at the end of completed steps of the surgical procedure. In some embodiments, the triggering event count can be set to a value other than 0, such as 1, 2, 3, or any other suitable integer. In various embodiments, the system can set the triggering event count based on a user input, input from a situational awareness module based on a detected step of a surgical procedure, or combinations thereof.

In one aspect, the system can detect partial triggering events, adjust the triggering event count based on the occurrences of the partial triggering events, and adjust the overlaid information on the display based on the triggering event count reaching or exceeding a triggering event threshold. In one example embodiment, the system can set the triggering event threshold to 3 partial triggering events. The system can set the triggering even count to 0 at the onset of a detected tissue manipulation step. The system can detect tissue tensions induced in the manipulated tissue against a tension threshold and add 1 to the triggering event count at each occurrence of the tension threshold being reached or exceeded. In the event the triggering event count reaches or exceeds the triggering event threshold, the system can adjust the overlaid information on the display accordingly, such as issuing a warning to the surgical staff or providing corrective actions to ensure the tension threshold is not reached or exceeded.

The ability to detect and count partial triggering events enables the system to track events that, in isolation, may be minor or inconsequential, but an accumulation of which could lead to an event that is major or consequential. For example, in the above-referenced tissue manipulation step, inducing tissue tension that exceeds a tension threshold in isolation may not overly harm the patient tissue, but multiple occurrences could result in torn, or damaged tissue.

In various embodiments, the partial triggering events could include additive triggering events that add to the triggering event count and negative triggering events that subtract from the triggering event count. In the above-described example embodiment regarding tissue tension induced by a tissue manipulator, tissue tension induced by the tissue manipulator can be an additive triggering even that adds 1 to the triggering event count. In some aspects, the system can track an amount of time that has elapsed since the occurrence of the last additive triggering event and compare the elapsed time to a threshold time. In the event that another additive triggering event is not induced by the time the elapsed time searches the threshold time, the system can detect this as a negative triggering event and subtract 1 from the triggering event count. In various embodiments, negative triggering events can be any event that diminishes, or takes away, from the impact caused by an additive triggering event. In one example embodiment, an additive triggering event can be a temperature threshold being reached or exceeded and a negative triggering event can be applying a temperature that is below the temperature threshold that cools the heated tissue. In other example embodiments, negative triggering events can be administering a drug, such as an injection, that negates, or takes away from, the impact caused by a positive triggering event.

In various embodiments, the additive and negative partial triggering events can have different weights. In one aspect, a first type of additive triggering event can add 1 to the triggering event count while a second type of additive triggering event can add 2 to the triggering event count. In one aspect, a first type of negative triggering event can subtract 1 from the triggering event count while a second type of negative triggering event can subtract 2 from the triggering event count. Any number of weights can be assigned to the partial triggering events, such as 1 to n, where n is the triggering event threshold (i.e., an additive triggering event count with a weight n will cause the triggering event threshold to be reached upon an occurrence thereof). The weights can be user defined, stored in a memory, be based on industry standards, or combinations thereof. In various embodiments, the partial triggering events can be values other than integers, such as 0.5, 1.5, or 1.8, as examples.

The ability to add and subtract from the triggering event count enables the system to track events that, in isolation, may be minor or inconsequential, but an accumulation of which could lead to an event that is major or consequential (additive triggering event). However, the system can also detect events that minimize, or diminish, the additive triggering events, and therefore, can take away from the triggering event count (negative triggering event). For example, in the above-referenced tissue manipulation step, inducing tissue tension that exceeds a tension threshold in isolation may not overly harm the patient tissue, but multiple occurrences could result in torn, or damaged tissue (additive triggering event). However, during the course surgical procedure that may last several hours, exceeding the tension threshold may be expected to occur a number of times that is greater than the triggering event threshold. This number of occurrence happening over a long period of time, however, may not result in serious harm to the tissue. Accordingly, the system can subtract from the triggering event count (negative triggering event) so as to maintain the triggering event count below the triggering event threshold and prevent the overlaid information to be adjusted where it may not be necessary.

In various embodiments, the system can detect cancelation triggering events that can cause the triggering event count to be reset. In one embodiment, the system can detect the number of occurrence in which tension is induced in tissue that exceeds a tension threshold during a step of the surgical procedure. The system can detect that the current tissue manipulation step of the surgical procedure has concluded and that a new step of the surgical procedure is occurring. Accordingly, the system can detect the completion of the tissue manipulation step as a cancelation triggering event, which resets the triggering event count, such as resetting the count back to 0.

In various embodiments, the system can monitor a plurality of triggering events that can have differing triggering event thresholds. In one embodiment, a first triggering event can have a first triggering event threshold, such as the system detecting 3 partial triggering events, and a second triggering event can have a second triggering event threshold, such as the system detecting 4 partial triggering events. In one aspect, having different triggering event thresholds allows the system to monitor partial triggering events that can have varying degrees of severity.

In various embodiments, the additive triggering events can be the same, or similar, additive triggering events. In one example embodiment, the triggering event threshold can be reached when the system detects the occurrence of the same three partial triggering events, such as tension in tissue reaching or exceeding a tension threshold. This allows the system to monitor for a specific type of event associated with a triggering event threshold and adjust the overlaid information in the event the specific type of event occurs a threshold number of times.

In various embodiments, the additive triggering events can be different additive triggering events. In one example embodiment, the triggering event threshold can be reached when the system detects the occurrence of three different types of additive triggering events, such as tension induced in tissue reaching a tension threshold, force applies to the tissue reaching a force threshold, and heat applied to the tissue reaching a temperature threshold. This allows the system to monitor different events that, on their own, may be inconsequential, but in combination, could damage the tissue. Therefore, the triggering event threshold can be reached upon the occurrence of multiple, independent partial triggering events, which can therefore cause the system to adjust the overlaid information on the display.

Figure 13:
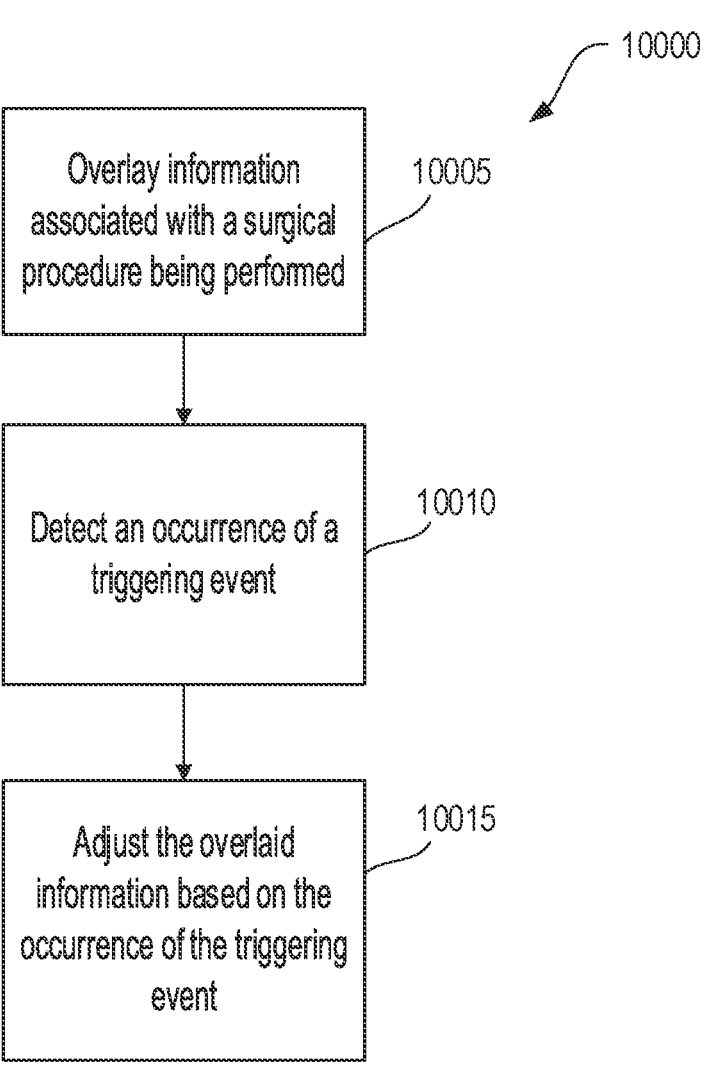
FIG. 13 illustrates a method for determining a display arrangement of surgical data competing for presentation onto a display that is showing a livestream of a surgical field, in accordance with at least one aspect of this disclosure.

FIG. 13 illustrates a flowchart showing operations of an example method 10000 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 10000 includes overlaying 10005, on the livestream, information associated with the surgical procedure. In one aspect, the control system can receive inputs from various modules, sensors, user input devices, a situational awareness module, as examples, and overlay information associated with these inputs on the display.

In various embodiments, the method 10000 includes detecting 10010 an occurrence of a triggering event. In one aspect, the triggering event can be any number of the triggering events described by the present disclosure that can result in the system adjusting overlaid information on the display.

In various embodiments, the method 10000 includes adjusting 10015 the overlaid information based on the occurrence of the triggering event. In one example embodiment, the adjustment can be the control system overlaying overlay information on the display associated with the triggering event. Any number of adjustments to the overlaid information can be made as described by the present disclosure.

Figure 14:
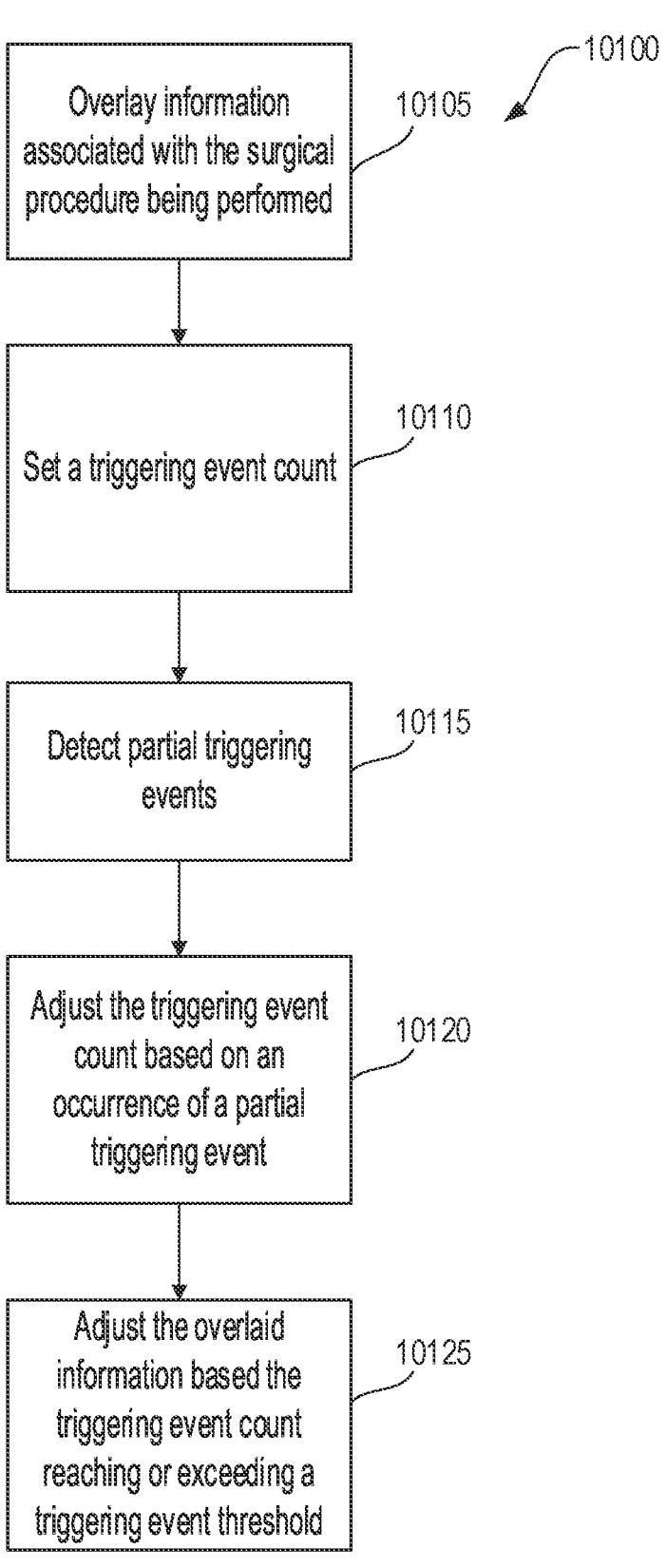
FIG. 14 illustrates a method for determining a display arrangement of surgical data competing for presentation onto a display that is showing a livestream of a surgical field, in accordance with at least one aspect of this disclosure.

FIG. 14 illustrates a flowchart showing operations of an example method 10100 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 10100 includes overlaying 10105, on the livestream, information associated with the surgical procedure. In one aspect, the control system can receive inputs from various modules, sensors, user input devices, a situational awareness module, as examples, and overlay information associated with these inputs on the display.

In various embodiments, the method 10100 further includes setting 10110 a triggering event count. In one aspect, the system can set the triggering event count to a value, such as 0, at the onset, or the beginning, of a step of the surgical procedure. In one aspect, the system can set the triggering event count to a value, such as 0, at the onset, or beginning, of the surgical procedure.

In various embodiments, the method 10100 further includes detecting 10115 partial triggering events. In one aspect, the system can detect partial triggering events, such as tissue tension reaching or exceeding a tension threshold, temperature of tissue reaching or exceeding a temperature threshold, or force applied to tissue reaching or exceeding a temperature threshold, as examples. The system can detect partial triggering events using any number of sensors, modules, imaging systems, or combinations thereof, as described elsewhere herein.

In various embodiments, the method 10100 further includes adjusting 10120 the triggering event count based on an occurrence of a partial triggering events. In one aspect, the system can index the triggering event count up 1 when an additive triggering event is detected. In one aspect, the system can index down 1 when a negative triggering event is detected. In one aspect, the system can reset the triggering event count back to the initial triggering event count, such as 0, upon the detection of a cancelation triggering event.

In various embodiments, the method 10100 further includes adjusting 10125 the overlaid information based on the triggering event count reaching or exceeding a triggering event threshold. In one aspect, the system can compare the triggering event count to a triggering event threshold and adjust the overlaid information based on the determination that the triggering event threshold has been reached or exceed. In one aspect, in the event of the triggering event threshold being reached or exceeded, the system can overlay a warning on the display indicating that the triggering event threshold has been reached or exceeded.

Figure 15:
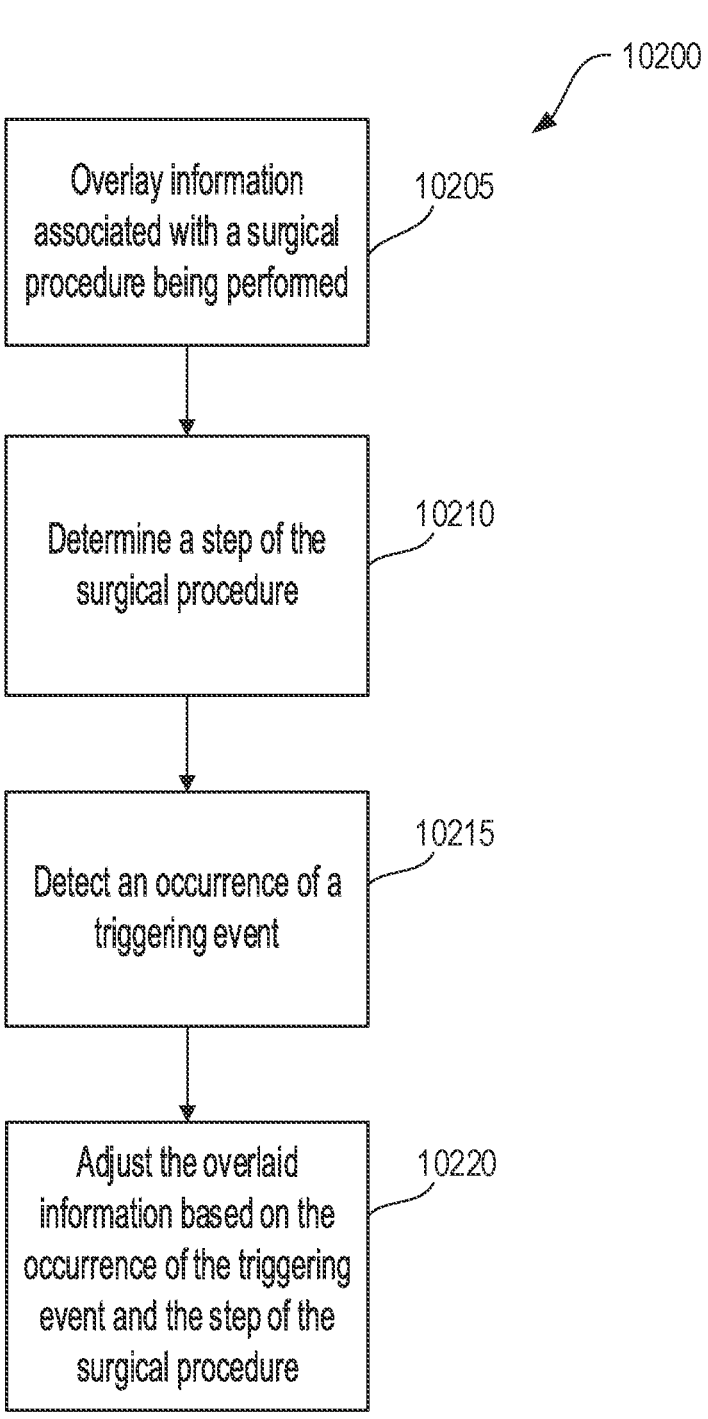
FIG. 15 illustrates a method for determining a display arrangement of surgical data competing for presentation onto a display that is showing a livestream of a surgical field, in accordance with at least one aspect of this disclosure.

FIG. 15 illustrates a flowchart showing operations of an example method 10100 for determining a display arrangement of surgical data competing for presentation onto a display, such as the display 6005, that is showing a livestream of a surgical field. In one aspect, the livestream can be captured by an imaging device, such as imaging device 6004, that is imaging a surgical field. The imaging device can be operably coupled to a control system, such as system 6000, which is also operably coupled to the display. The control system can transmit the livestream of the surgical field from the imaging device to the display such that surgical personnel can view the livestream on the display.

In various embodiments, the method 10200 includes overlaying 10205, on the livestream, information associated with the surgical procedure. In one aspect, the control system can receive inputs from various modules, sensors, user input devices, a situational awareness module, as examples, and overlay information associated with these inputs on the display.

In various embodiments, the method 10200 further includes determining 10210 a step of the surgical procedure. In one aspect, the system can determine a step of the surgical procedure, such as a step currently taking place, or that is soon to take place, based on any number of inputs provided to the system. In one aspect, the system can determine the step of the surgical procedure using a situational awareness module that can receive various amount of information from sensors, modules, and devices, for the purposes of determining the step of the surgical procedure.

In various embodiments, the method 10200 further includes detecting 10215 an occurrence of a triggering event. In one aspect, the triggering event can be any number of the triggering events described by the present disclosure that can result in the system adjusting overlaid information on the display.

In various embodiments, the method 10200 further includes adjusting 10120 the overlaid information based on the occurrence of the triggering event and the step of the surgical procedure. In one example embodiment, the system can determine that an upcoming step of the surgical procedure is a surgical stapling operation and the triggering event is the completion of a step of the surgical procedure. The system can adjust the display to overlay information about the upcoming step of the surgical procedure, such as the type of staple cartridge that is needed to complete the step of the surgical procedure. In another example embodiment, the system can determine that the currently step of the surgical procedure is a tissue manipulation step and the triggering event is a force being applied to the tissue reaching or exceeding a force threshold. The system can adjust the display to overlay information related to the threshold being reached or exceeded, such as informing the user that less pressure should be applied.

Various additional aspects of the subject matter described herein are set out in the following numbered examples:

Example 1: A surgical system comprising an imaging device, a display configured to show a livestream of a surgical field of a surgical procedure, wherein the livestream is captured by the imaging device, and a control system operably coupled to the imaging device and the display, wherein the control system is configured to overlay, on the livestream, information associated with the surgical procedure, detect an occurrence of a triggering event, and adjust the overlaid information based on the occurrence of the triggering event.

Example 2: The surgical system of Example 1, wherein control system is configured to monitor a parameter associated with a patient to which the surgical procedure is being performed, wherein the triggering event comprises a value of the parameter reaching or exceeding a parameter threshold.

Example 3: The surgical system of Examples 1 or 2, wherein control circuit is configured to monitor a parameter associated with a patient to which the surgical procedure is being performed, wherein the triggering event comprises a rate of change of a value of the parameter reaching or exceeding a rate of change threshold.

Example 4: The surgical system of any one of Examples 1-3, further comprising a surgical device associated with a surgeon, wherein the triggering event comprises an event induced by the surgical device.

Example 5: The surgical system of any one of Examples 1-4, further comprising a first surgical device associated with a surgeon, a second surgical device unassociated with the surgeon, wherein the triggering event comprises an event induced by the second surgical device.

Example 6: The surgical system of any one of Examples 1-5, wherein the triggering event comprises a triggering event threshold, wherein the control system is further configured to set a triggering event count, detect partial triggering events, and adjust the triggering event count based on an occurrence of a partial triggering event, wherein detecting the occurrence of the triggering event comprises detecting the triggering event count reaching or exceeding the triggering event threshold.

Example 7: The surgical system of Example 6, wherein the partial triggering events comprise additive triggering events and negative triggering events, and wherein adjusting the triggering event count comprises adding to the triggering event count based on an occurrence of an additive triggering event and subtracting from the triggering event count based on an occurrence of a negative triggering event.

Example 8: The surgical system of any one of Examples 1-7, further comprising a memory storing data associated with objects, wherein the control system is further configured to identify an object in the livestream and compare the object to the data associated with objects stored in the memory, wherein the triggering event comprises the object being identified from the comparison.

Example 9: The surgical system of any one of Examples 1-8, further comprising an interactive sensor, wherein the triggering event comprises a user interacting with the interactive sensor.

Example 10: The surgical system of any one of Examples 1-9, further comprising a surgical instrument comprising an end effector, wherein the control system is further configured to monitor a position of the end effector, and wherein the triggering event comprises the end effector reaching a location.

Example 11: The surgical system of any one of Examples 1-10, wherein the control system is configured to monitor a position of a user, and wherein the triggering event comprises the user reaching a location.

Example 12: The surgical system of Example 11, wherein adjusting the overlaid information comprises overlaying information associated with the location.

Example 13: The surgical system of Example 12, wherein the overlaid information associated with the location comprises information associated with the surgical procedure.

Example 14: The surgical system of Examples 12 or 13, further comprising a situational awareness module operably coupled to the control system, wherein the control system is further configured to determine, by the situational awareness module, a step of the surgical procedure, and wherein the overlaid information associated with the location comprises information associated with the step of the surgical procedure.

Example 15: The surgical system of any one of Examples 12-14, wherein the overlaid information associated with the location comprises information based on user input.

Example 16: The surgical system of any one of Examples 1-15, further comprising a situational awareness module operably coupled to the control system, wherein the control system is further configured to determine, by the situational awareness module, a step of the surgical procedure and determine a component required to perform the step of the surgical procedure, wherein the triggering event comprises the control system determining the component required to perform the step of the surgical procedure, and wherein adjusting the overlaid information comprises providing directional information for where the component can be located.

Example 17: The surgical system of any one of Examples 1-16, wherein the display comprises a first display, wherein the surgical system further comprises a second display, and wherein adjusting the overlaid information comprises moving overlaid information from the first display to the second display.

Example 18: A surgical system comprising an imaging device, a display configured to show a livestream of a surgical field of a surgical procedure, wherein the livestream is captured by the imaging device, and a control system operably coupled to the imaging device and the display, wherein the control system is configured to overlay, on the livestream, information associated with the surgical procedure, set a triggering event count, detect partial triggering events, adjust the triggering event count based on an occurrence of a partial triggering event, and adjust the overlaid information based on the triggering event count reaching or exceeding a triggering event threshold.

Example 19: The surgical system of Example 18, wherein the partial triggering events comprise additive triggering events and negative triggering events, and wherein adjusting the triggering event count comprises adding to the triggering event count based on an occurrence of an additive triggering event and subtracting from the triggering event count based on an occurrence of a negative triggering event.

Example 20: A surgical system comprising an imaging device, a display configured to show a livestream of a surgical field of a surgical procedure, wherein the livestream is captured by the imaging device, a situational awareness module, and a control system operably coupled to the imaging device, the display, and the situational awareness module, wherein the control system is configured to overlay, on the livestream, information associated with the surgical procedure, determine, by the situational awareness module, a step of the surgical procedure, detect an occurrence of a triggering event, and adjust the overlaid information based on the occurrence of the triggering event and the step of the surgical procedure.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of this disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a control circuit, a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A surgical system, comprising:
an imaging device;
a display configured to show a livestream of a surgical field of a surgical procedure, wherein the livestream is captured by the imaging device; and
a control system operably coupled to the imaging device and the display, wherein the control system is configured to:
overlay, on the livestream, information associated with the surgical procedure;
set a triggering event count representing a number of detected partial triggering events within the surgical field;
detect a plurality of partial triggering events, wherein the plurality of partial triggering events comprise a negative triggering event;
determine an amount by which to decrement the triggering event count based on the negative triggering event;

adjust the triggering event count, based at least in part on the amount by which to decrement the triggering event count, by incrementing or decrementing the triggering event count based on the detected plurality of partial triggering events; and
detect the occurrence of the triggering event based on detecting the triggering event count reaching or exceeding a triggering event threshold.

2. The surgical system of claim 1, wherein control system is configured to monitor a parameter associated with a patient to which the surgical procedure is being performed, wherein the triggering event comprises a value of the parameter reaching or exceeding a parameter threshold.

3. The surgical system of claim 1, wherein control circuit is configured to monitor a parameter associated with a patient to which the surgical procedure is being performed, wherein the triggering event comprises a rate of change of a value of the parameter reaching or exceeding a rate of change threshold.

4. The surgical system of claim 1, further comprising a surgical device associated with a surgeon, wherein the triggering event comprises an event induced by the surgical device.

5. The surgical system of claim 1, further comprising:
a first surgical device associated with a surgeon; and
a second surgical device unassociated with the surgeon;
wherein the triggering event comprises an event induced by the second surgical device.

6. The surgical system of claim 1, wherein the partial triggering events further comprise additive triggering events, and wherein adjusting the triggering event count, based at least in part on the amount by which to decrement the triggering event count, comprises:
adding to the triggering event count based on an occurrence of an additive triggering event; and
subtracting from the triggering event count based on an occurrence of a negative triggering event.

7. The surgical system of claim 1, further comprising a memory storing data associated with objects, wherein the control system is further configured to:
identify an object in the livestream; and
compare the object to the data associated with objects stored in the memory;
wherein the triggering event comprises the object being identified from the comparison.

8. The surgical system of claim 1, further comprising an interactive sensor, wherein the triggering event comprises a user interacting with the interactive sensor.

9. The surgical system of claim 1, further comprising a surgical instrument comprising an end effector, wherein the control system is further configured to monitor a position of the end effector, and wherein the triggering event comprises the end effector reaching a location.

10. The surgical system of claim 1, wherein the control system is configured to monitor a position of a user, and wherein the triggering event comprises the user reaching a location.

11. The surgical system of claim 10, wherein adjusting the overlaid information comprises overlaying information associated with the location.

12. The surgical system of claim 11, wherein the overlaid information associated with the location comprises information associated with the surgical procedure.

13. The surgical system of claim 11, wherein the control system is further configured to determine a step of the surgical procedure, and wherein the overlaid information associated with the location comprises information associated with the step of the surgical procedure.

14. The surgical system of claim 11, wherein the overlaid information associated with the location comprises information based on user input.

15. The surgical system of claim 1, wherein the control system is further configured to:

determine a step of the surgical procedure; and determine a component required to perform the step of the surgical procedure; wherein the triggering event comprises the control system determining the component required to perform the step of the surgical procedure; and wherein adjusting the overlaid information comprises providing directional information for where the component can be located.

16. The surgical system of claim 1, wherein the ray comprises a first display, wherein the surgical system further comprises a second display, and wherein adjusting the overlaid information comprises moving overlaid information from the first display to the second display.

17. A surgical system, comprising:

an imaging device;

a display configured to show a livestream of a surgical field of a surgical procedure, wherein the livestream is captured by the imaging device; and a control system operably coupled to the imaging device, and the display wherein the control system is configured to:

overlay, on the livestream, information associated with the surgical procedure;

determine a step of the surgical procedure;

set a triggering event count representing a number of detected partial triggering events within the surgical field;

detect a plurality of partial triggering events, wherein the plurality of partial triggering events comprise a negative triggering event;

determine an amount by which to decrement the triggering event count based on the negative triggering event;

adjust the triggering event count, based at least in part on the amount by which to decrement the triggering event count, by incrementing or decrementing the triggering event count based on the detected plurality of partial triggering events;

detect the occurrence of the triggering event based on detecting the triggering event count reaching or exceeding a triggering event threshold.

18. The surgical system of claim 17, wherein the partial triggering events comprise additive triggering events, and wherein adjusting the triggering event count, based at least in part on the amount by which to decrement the triggering event count, comprises:

adding to the triggering event count based on an occurrence of an additive triggering event; and subtracting from the triggering event count based on an occurrence of a negative triggering event.

* * * * *